(12) United States Patent
Goldman

(10) Patent No.: US 10,279,051 B2
(45) Date of Patent: May 7, 2019

(54) NON-HUMAN MAMMAL MODEL OF HUMAN DEGENERATIVE DISORDER, USES THEREOF, AND METHOD OF TREATING HUMAN DEGENERATIVE DISORDER

(71) Applicant: University of Rochester, Rochester, NY (US)

(72) Inventor: Steven A. Goldman, Webster, NY (US)

(73) Assignee: University of Rochester, Rochester, NY (US)

( * ) Notice: Subject to any disclaimer, the term of this patent is extended or adjusted under 35 U.S.C. 154(b) by 62 days.

(21) Appl. No.: 15/429,585

(22) Filed: Feb. 10, 2017

(65) Prior Publication Data
US 2017/0182098 A1 Jun. 29, 2017

Related U.S. Application Data

(62) Division of application No. 14/701,245, filed on Apr. 30, 2015, now Pat. No. 9,724,432.

(51) Int. Cl.
*C12N 5/07* (2010.01)
*A61K 35/30* (2015.01)
(Continued)

(52) U.S. Cl.
CPC ...... *A61K 49/0008* (2013.01); *A01K 67/0271* (2013.01); *A61K 35/30* (2013.01);
(Continued)

(58) Field of Classification Search
CPC .............. G01N 33/5085; G01N 33/50; G01N 2800/2814; G01N 2800/2821; G01N 2800/2835; G01N 2800/28; A61K 45/06; A61K 49/0008; A61K 35/30; A61K 35/545; A01K 67/0271; A01K 2207/12;
(Continued)

(56) References Cited

U.S. PATENT DOCUMENTS 3,753,357 A    8/1973  Schwartz
4,199,022 A    4/1980  Senkan et al.
(Continued)

FOREIGN PATENT DOCUMENTS

EP    2379711 B1    11/2016
EP    2499238 B1    8/2017
(Continued)

OTHER PUBLICATIONS

Higuchi et al. Transgenic Mouse Model of Tauopathies with Glial Pathology and Nervous System Degeneration. Neuron (2002), v35, p. 433-446. (Year: 2002).*
(Continued)

*Primary Examiner* — Sean C. Barron
(74) *Attorney, Agent, or Firm* — Pepper Hamilton LLP

(57) ABSTRACT

The present application relates to a non-human mammal model of a human neurodegenerative disorder, methods of producing the non-human mammal model, and methods of using the non-human mammal model to identify agents suitable for treating a neurodegenerative disorder. The present application also relates to methods of treating neurodegenerative disorders and restoring normal brain interstitial potassium levels.

8 Claims, 9 Drawing Sheets

(51) Int. Cl.
  *A61K 45/06* (2006.01)
  *A61K 49/00* (2006.01)
  *C12N 5/079* (2010.01)
  *G01N 33/50* (2006.01)
  *A01K 67/027* (2006.01)
  *A61K 35/545* (2015.01)

(52) U.S. Cl.
  CPC .......... *A61K 35/545* (2013.01); *A61K 45/06* (2013.01); *C12N 5/06* (2013.01); *C12N 5/0622* (2013.01); *G01N 33/50* (2013.01); *G01N 33/5085* (2013.01); *A01K 2207/12* (2013.01); *A01K 2207/15* (2013.01); *A01K 2227/105* (2013.01); *A01K 2267/0318* (2013.01); *G01N 2800/28* (2013.01); *G01N 2800/2814* (2013.01); *G01N 2800/2821* (2013.01); *G01N 2800/2835* (2013.01)

(58) Field of Classification Search
  CPC ...... A01K 2267/0318; A01K 2227/105; A01K 2207/15; C12N 5/06; C12N 5/0622
  See application file for complete search history.

(56) References Cited

U.S. PATENT DOCUMENTS

| | | | |
|---|---|---|---|
| 4,559,298 A | 12/1985 | Fahy | |
| 5,026,365 A | 6/1991 | Rossini | |
| 5,082,670 A | 1/1992 | Gage et al. | |
| 6,235,527 B1 | 5/2001 | Rao et al. | |
| 6,245,564 B1 | 6/2001 | Goldman et al. | |
| 6,361,996 B1 | 3/2002 | Rao et al. | |
| 6,497,872 B1 | 12/2002 | Weiss et al. | |
| 6,692,957 B2 | 2/2004 | Goldman et al. | |
| 6,734,015 B1 | 5/2004 | Rao et al. | |
| 6,787,353 B1 | 9/2004 | Rao et al. | |
| 6,830,927 B2 | 12/2004 | Rao et al. | |
| 6,852,532 B2 | 2/2005 | Mayer-Proschel et al. | |
| 6,900,054 B2 | 5/2005 | Rao et al. | |
| 7,037,720 B2 | 5/2006 | Rao et al. | |
| 7,150,989 B2 | 12/2006 | Goldman et al. | |
| 7,214,372 B2 | 5/2007 | Rao et al. | |
| 7,517,521 B2 | 4/2009 | Mayer-Proschel et al. | |
| 7,524,491 B2 | 4/2009 | Goldman et al. | |
| 7,595,194 B2 | 9/2009 | Rao et al. | |
| 7,795,021 B2 | 9/2010 | Rao et al. | |
| 8,168,174 B2 | 5/2012 | Mayer-Proschel et al. | |
| 8,206,699 B2 | 6/2012 | Goldman et al. | |
| 8,227,247 B2 | 7/2012 | Zhang et al. | |
| 8,263,402 B1 | 9/2012 | Goldman et al. | |
| 8,642,332 B2 | 2/2014 | Goldman et al. | |
| 8,658,424 B2 | 2/2014 | Zhang et al. | |
| 8,669,048 B2 | 3/2014 | Reijo Pera | |
| 8,673,292 B2 | 3/2014 | Rao et al. | |
| 8,709,807 B2 | 4/2014 | Mayer-Proschel et al. | |
| 9,371,513 B2 | 6/2016 | Goldman et al. | |
| 9,709,553 B2 | 7/2017 | Goldman et al. | |
| 2002/0012903 A1 | 1/2002 | Goldman et al. | |
| 2002/0061586 A1 | 5/2002 | Goldman et al. | |
| 2003/0049234 A1 | 3/2003 | Goldman et al. | |
| 2003/0223972 A1 | 12/2003 | Goldman et al. | |
| 2004/0029269 A1 | 2/2004 | Goldman et al. | |
| 2004/0253719 A1 | 12/2004 | Goldman et al. | |
| 2005/0084963 A1 | 4/2005 | Chan-Ling | |
| 2008/0213232 A1 | 9/2008 | Grumet | |
| 2008/0226609 A1 | 9/2008 | Proschel et al. | |
| 2008/0233610 A1 | 9/2008 | Thomsan et al. | |
| 2010/0156778 A1 | 6/2010 | Yamagishi | |
| 2010/0159595 A1 | 6/2010 | Zhang et al. | |
| 2011/0059055 A1 | 3/2011 | Goldman et al. | |
| 2011/0200568 A1 | 8/2011 | Ikeda et al. | |
| 2012/0100113 A1 | 4/2012 | Tesar et al. | |
| 2012/0100615 A1 | 4/2012 | Tesar et al. | |
| 2012/0156778 A1 | 6/2012 | Egusa et al. | |
| 2012/0177614 A1 | 7/2012 | Kido | |
| 2012/0207744 A1 | 8/2012 | Medlein et al. | |
| 2012/0230963 A1 | 9/2012 | Sandrock et al. | |
| 2012/0276070 A1 | 11/2012 | Musick | |
| 2012/0276636 A1 | 11/2012 | Nakagawa et al. | |
| 2013/0004467 A1 | 1/2013 | Goldman et al. | |
| 2015/0328339 A1 | 11/2015 | Goldman et al. | |
| 2015/0352154 A1 | 12/2015 | Goldman et al. | |
| 2016/0264937 A1 | 9/2016 | Goldman et al. | |
| 2017/0159015 A1 | 6/2017 | Goldman et al. | |
| 2017/0182098 A1 | 6/2017 | Goldman et al. | |
| 2017/0198255 A1 | 7/2017 | Goldman et al. | |
| 2017/0209494 A1 | 7/2017 | Goldman et al. | |

FOREIGN PATENT DOCUMENTS

| | | |
|---|---|---|
| JP | 2011-155978 A | 8/2011 |
| WO | WO 92/04033 | 3/1992 |
| WO | WO92/04033 | 3/1992 |
| WO | WO 94/10292 A1 | 5/1994 |
| WO | WO 98/32879 A1 | 7/1998 |
| WO | WO 99/49014 A1 | 9/1999 |
| WO | WO 01/46384 A2 | 6/2001 |
| WO | WO 01/178753 A2 | 10/2001 |
| WO | WO 03/07017 A2 | 8/2003 |
| WO | WO 2004007696 A2 | 1/2004 |
| WO | WO2007/069666 | 6/2007 |
| WO | WO 2007069666 | 6/2007 |
| WO | WO2008/118820 | 10/2008 |
| WO | WO 200818820 | 10/2008 |
| WO | WO2009/006930 | 1/2009 |
| WO | WO2009/006997 | 1/2009 |
| WO | WO2009/007852 | 1/2009 |
| WO | WO 2009006930 | 1/2009 |
| WO | WO 2009006997 | 1/2009 |
| WO | WO 2012095730 A1 | 7/2012 |
| WO | WO2014/124087 | 8/2014 |
| WO | WO 2014124087 | 8/2014 |

OTHER PUBLICATIONS

Brettschneider et al. Sequential distribution of pTDP-43 pathology in behavioral variant frontotemporal dementia (bvFTD). Acta Neuropathol (epub Jan. 10, 2014), v127(3), p. 423-439. (Year: 2014).*
Zhang et al. White matter damage in frontotemporal dementia and Alzheimer's disease measured by diffusion MRI. Brain (2009), v132(9), p. 2579-2592. (Year: 2009).*
Jicha et al. Management of frontotemporal dementia: targeting symptom management in such a heterogeneous disease requires a wide range of therapeutic options. Neurodegener Dis Manag (2011), v1(2), 26 page manuscript. (Year: 2011).*
Benraiss et al., "Cellular Therapy and Induced Neuronal Replacement for Huntington's Disease," *Neuro Ther*. 8(4): 577-590 (2011).
Cambi et al., *Neurochem. Res*. 19:1055-60 (1994).
Feng et al., *Nat. Cell Biol*. 11:197-203 (2009).
Giorgetti et al., "Generation of Induced Pluripotent Stem Cells from Human Cord Blood Cells with only Two Factors: Oct. 4 and Sox2," *Nat. Protocol*. 5(4):811-820 (2010).
Gloster et al., *J. Neurosci*. 14:7319-30 (1994).
Gruber, *Transplantation* 54:1-11 (1992).
Hanna et al., *Cell* 133(2):250-264 (2008).
Holst et al., *J. Biol. Chem*. 269:22245-52 (1994).
Huangfu et al., *Nat. Biotechnol*. 26:1269-1275 (2008).
Keyoung et al., "High-Yield Selection and Extraction of Two Promoter-Defined Phenotypes of Neural Stem Cells from the Fetal Human Brain," *Nat. Biotechnol*. 19:843-850 (2001).
Kim et al., *Cell* 136(3):411-419 (2009).
Kim et al., *Nature* 454:646-650 (2008).
Klapstein et al.,"Electrophysiological and Morphological Changes in Striatal Spiny Neurons in R6/2 Huntington's Disease Transgenic Mice," *J Neurophysiol*. 86(6): 2667-2677 (2001).
Krebs et al., *J. Virol*. 69:2434-42 (1995).
Liu et al., *Gene* 171:307-08 (1996).
Meissner et al. *Nat. Biotech*. 25:1177-1181 (2007).

(56) References Cited

OTHER PUBLICATIONS

Mombaerts et al., *Cell* 68:869-877 (1992).
Nakagawa et al., *Nat. Biotechnol.* 26:101-106 (2007).
Nisenbaum et al., "Potassium Currents Responsible for Inward and Outward Rectification in Rat Neostriatal Spiny Projection Neurons," *J. Neurosci.* 15:4449-446.
Nunes et al., "Identification and Isolation of Multipotential Neural Progenitor Cells from the Adult Human White Matter," *Soc. Neurosci. Abstr.* (2001).
Okita. et al., *Nature* 448:313-317 (2007).
Park et al. *Nature* 451:141-146 (2008).
Park et al., "Analysis of Upstream Elements in the HuC Promoter Leads to the Establishment of Transgenic Zebrafish with Fluorescent Neurons," *Dev. Biol.* 227(2): 279-93 (2000).
Scherer et al., *Neuron* 12:1363-75 (1994).
Schultz et al., *Transplantation* 76:1036-42 (2003).
Shi et al., *Cell Stem Cell* 3(5):568-574 (2008).
Shin et al., "Expression of Mutant Huntingtin in Glial Cells Contributes to Neuronal Excitotoxicity, "*J Cell Biol.* 171:1001-1012 (2005).
Shinkai et al., *Cell* 68:855-867 (1992).
Sim et al., "CD140a Identifies a Population of Highly Myelinogenic, Migration-Competent and Efficiently Engrafting Human Oligodendrocyte Progenitor Cells," *Nat Biotechnol* 29(10): 934-941 (2011).
Smithies et al. *Nature* 317:230-234 (1985).
Takahashi and Yamanaka, *Cell* 126:663-676 (2006).
Takahashi et al., *Cell* 131:861-872 (2007).
Verkhratsky et al., Astrogliopathology in Neurological, Neurodevelopmental and Psychiatric Disorders, *Neurobiol Dis*. pii: S0969-9961(15)00103-5 (2015).
Windrem et al., "Fetal and Adult Human Oligodendrocyte Progenitor Cell Isolates Myelinate the Congenitally Dysmyelinated Brain," *Nat. Med.* 10:93-97 (2004).
Windrem et al., "Neonatal Chimerization with Human Glial Progenitor Cells can both Remyelinate and Rescue the Otherwise Lethally Hypomyelinated Shiverer Mouse," *Cell Stem Cell* 2:553-565 (2008).
Wrabetz et al., *J. Neurosci. Res.* 36:455-71 (1993).
Yao et al., "Neural Specificity of ELAV Expression: Defining a *Drosophila* Promoter for Directing Expression to the Nervous System," *J. Neurochem.* 63(1): 41-51 (1994).
Yu et al. *Science* 318:1917-1920 (2007).
Zhao et al., *Cell Stem Cell* 3:475-479 (2008).
Zufferey et al., "Woodchuck Hepatitis Virus Posttranscriptional Regulatory Element Enhances Expression of Transgenes Delivered by Retroviral Vectors," *J. Virol.* 73:2886-2892 (1999).
Goldman et al., "Glial Progenitor Cell-Based Treatment and Modeling of Neurological Disease," Science 338(6106):491-495 (2012).
Windrem et al., "Neonatal Chimerization with Human Glial Progenitor Cells Can Both Remyelinate and Rescue the Otherwise Lethally Hypomyelinated Shiverer Mouse," Cell Stem Cell 2(6):553-565 (2008).
Walker, F., "Huntington's Disease," Lancet. 369(9557):218-28 (2007).
Reitz et al., "Alzheimer Disease: Epidemiology, Diagnostic Criteria, Risk Factors and Biomarkers," Biochem Pharmacol. 88(4):640-51 (2014).
Lobsiger et al., "Glial Cells as Intrinsic Components of Non-cell-autonomous Neurodegenerative Disease," Nat Neurosci. 10(11):1355-60 (2007).
Southwell et al., "A Fully Humanized Transgenic Mouse Model of Huntington Disease," Hum Mol Genet. 22(1):18-34 (2013).
"Frontotemporal Dementia (FTD)," Alzheimer's Association pp. 1-4 (2012).
Abeyta et al., "Unique Gene Expression Signature of Independently-Derived Human Embryonic Stem Cell Lines," *Human Molecular Genetics* 13(6):601-608 (2004).
Akiyama et al., "Transplantation of Clonal Neural Precursor Cells Derived from Adult Human Brain Establishes Functional Peripheral Myelin in the Rat Spinal Cord," *Exp. Neuro.* 167:27-39 (2001).

Abbaszadeh et al., "Bone Marrow Stromal Cell Transdifferentiation into Oligodendrocyte-Like Cells Using Triiodothyronine as an Inducer with Expression of Platelet-Derived Growth Factor Alpha as a Maturity Marker," *Iranian Biomedical Journal* 17(2):62-70 (2013).
Alenzi et al., "Stem Cells: Biology and Clinical Potential," *African Journal of Biotechnology* 10(86):19929-19940 (2011).
Allegrucci et al., "Differences Between Human Embryonic Stem Cell Lines," *Human Reproduction Update*, Advanced Access published on Aug. 26, 2006, pp. 1-18.
Alsanie et al., "Human Embryonic Stem Cell-Derived Oligodendrocytes: Protocols and Perspectives," *Stem Cells and Developments* 22(18):2459-2476 (2013).
Ariano et al., "Striatal Potassium Channel Dysfunction in Huntington's Disease Transgenic Mice," *J Neurophysiol.* 93(5): 2565-2574 (2005).
Armstrong et al., "Pre-Oligodendrocytes from Adult Human CNS," *J. Neurosci.* 12(4):1538-47 (1992).
Ashcroft et al., "Voltage-gated $K^+$ Channels," in *Ion Channels and Disease*. San Diego, CA: Academic: 97-125 (2000).
Auvergne et al., "Transcriptional Differences Between Normal and Glioma-Derived Glial Progenitor Cells Identify a Core Set of Dysregulated Genes," *Cell Reports* 3:2127-2141 (2013).
Ballanyi et al., "Ion Activities and Potassium Uptake Mechanisms of Glial Cells in Guinea-Pig Olfactory Cortex Slices," *Journal of physiol.* 382: 159-174 (1987).
Bargas et al., "An Early Outward Conductance Modulates the Firing Latency and Frequency of Neostriatal Neurons of the Rat Brain," *Exp. Brain Res.* 75:146-156 (1989).
Bargas et al., "Electrotonic Properties of Neostriatal Neurons are Modulated by Extracellular Potassium," *Exp. Brain Res.* 72:390-398 (1988).
Bellin et al., "Induced Pluripotent Stem Cells: The new Patient?," *Nature Reviews Molecular Cell Biology* 13:713-726 (2012).
Ben-Hur and Goldman, "Prospects of Cell Therapy for Disorders of Myelin," *Ann. N.Y. Acad. Sci.* 1142:218-249 (2008).
Benraiss et al., "Cellular Therapy and Induced Neuronal Replacement for Huntington's Disease," *Neurotherapeutics* 8:577-590 (2011).
Benraiss et al., "Sustained Mobilization of Endogenous Neural Progenitors Delays Disease Progression in a Transgenic Model of Huntington's Disease," *Cell Stem Cell* 12:787-799 (2013).
Berry et al., "Cytology and Lineage of NG2-Positive Glia," *Journal of Neurocytology* 31:457-467 (2002).
Bertil Hille, *Ionic Channels of Excitable Membranes*, Ch. 5 (3d ed., Sinauer 2001).
Bjorklund and Stenevi (eds), *Neural Grafting in the Mammalian CNS*, Ch. 3-8, Elsevier, Amsterdam (1985).
Blakemore et al., "Extensive Oligodendrocyte Remyelination Following Injection of Cultured Central Nervous System Cells into Demyelinating Lesions in Adult Central Nervous System," *Dev. Neurosci.* 10:1-11 (1988).
Bockenhauer et al., "Epilepsy, Ataxia, Sensorineural Deafness, Tubulopathy, and KCNJ10 Mutations," *The New England Journal of Medicine* 360(19): 1960-1970 (2009).
Bradley et al., "Derivation of Huntington's Disease-Affected Human Embryonic Stem Cell Lines," *Stem Cells Dev* 20(3):495-502 (2011).
Burridge et al., "A Universal System for Highly Efficient Cardiac Differentiation of Human Induced Pluripotent Stem Cells that Eliminates Interline Variability," *PLoS ONE* 6(4):e18293, 1-16 (2011).
Cai et al., "Generation of Human Induced Pluripotent Stem Cells from Umbilical Cord Matrix and Amniotic Membrane Mesenchymal Cells," *J. Biol. Chem.* 285(15):112227-11234 (2010).
Cambi et al., "Transcriptiomnal Regulation of the Rat PLP Promoter in Primary Cultures of Oligodendrocytes," *Neurochem Res.* 19:1055-1060 (1994).
Cao et al., "Stem Cell Repair of Central Nervous System Injury," *Journal of Neuroscience Research* 68:501-510 (2002).
Chin et al., "Induced Pluripotent Stem Cells and Embryonic Stem Cells are Distinguished by Gene Expression Signatures," *Cell Stem Cell* 5(1):111-123 (2009).
Chmielnicki et al., "Adenovirally Expressed Noggin and Brain-Derived Neurotrophic Factor Cooperate to Induce New Medium

(56) References Cited

OTHER PUBLICATIONS

Spiny Neurons from Resident Progenitor Cells in the Adult Striatal Ventricular Zone," *J. Neurosci.* 24(9):2133-2142 (2004).
Cho et al., "Induction of Neostriatal Neurogenesis Slows Disease Progression in a Transgenic Murine Model of Huntington Disease," *J. Clin. Invest.* 117(10):2889-2902 (2007).
Chua et al., "Neural progenitors, Neurons and Oligodendrocytes from Human Umbilical Cord Blood Cells in a Serum-Free, Feeder-Free Cell Culture," *Biochem. Biopyhs. Res. Comm.* 379:217-221 (2009).
Chung et al., "Human Embryonic Stem Cell Lines Generated Without Embryo Destruction," *Cell Stem Cell* 2(2):113-117 (2008).
Communication for European Patent Application No. 09743660.4 (dated Mar. 27, 2014).
Cook et al., "Regulation of Rodent Myelin Proteolipid Protein Gene Expression," *Neurosci. Lett.* 137(1):56-60 (1992).
Crang et al., "The Demonstration by Transplantation of the Very Restricted Remyelinating Potential of Post-Mitotic Oligodendrocytes," *J.* Neurocytol. 27(7):541-553 (1998).
Database Accession No. PREV200100486585 (2001).
Dennis et al., "DAVID: Database for Annotation, Visualization, and Integrated Discovery," *Genome Biol.* 4(5):P3 (2003).
Di Giorgio et al., "Non-Cell Autonomous Effect of Glia on Motor Neurons in an Embryonic Stem Cell-Based ALS Model," *Nat. Neurosci.* 10(5):608-614 (2007).
Di Giorgio et al., "Human Embryonic Stem Cell-Derived Motor Neurons are Sensitive to the Toxic Effect of Glial Cells Carrying an ALS-Causing Mutation," *Cell Stem Cell* 3(6):637-648 (2008).
Djukic et al., "Conditional Knock-Out of Kir4.1 Leads to Glial Membrane Depolarization, Inhibition of Potassium and Glutamate Uptake, and Enhanced Short-Term Synaptic Potentiation," *J. Neurosci.* 27(42):11354-11365 (2007).
Emerich et al., "Recent Efforts to Overcome the Blood-Brain Barrier for Drug Delivery," *Exp. Opin. Ther. Patents* 10(3):279-287 (2000).
Espinosa De Los Monteros et al., "Remyelination of the Adult Demyelinated Mouse Brain by Grafted Oligodendrocyte Progenitors and the Effect of B-104 Cografts," *Neurochemical Res.* 26(6):673-682 (2001).
European Search Report for European Patent Application No. 09743660.4 (dated Dec. 11, 2011).
Feng et al., "Reprogramming of Fibroblasts into Induced Pluripotent Stem Cells with Orphan Nuclear Receptor Esrrb," *Nat. Cell Biol.* 11:197-203 (2009).
Franklin, "Why Does Remyelination Fail in Multiple Sclerosis?" *Nature Rev. Neurosci.* 3(9):705-714 (2002).
Frontotemporal Dementia, Internet Article by the Alzheimer's Association, 4 pages (2012).
Gallo et al., "Oligodendrocyte Progenitor Cell Proliferation and Lineage Progression are Regulated by Glutamate Receptor-Mediated $K^+$ Channel Block," *J. Neurosci.* 16(8): 2659-2670 (1996).
Gensert et al., "Endogenous Progenitors Remyelinate Demyelinated Axons in the Adult CNS," *Neuron* 19:197-203 (1997).
Gentleman et al., "Bioconductor: Open Software Development for Computational Biology and Bioinformatics," *Genome Biol.* 5(10):R80-R80. 16 (2004).
Giorgetti et al., "Generation of Induced Pluripotent Stem Cells from Human Cord Blood Cells with Only Two Factors: Oct14 and Sox2," *Nat. Protocol.* 5(4):811-820 (2010).
Gloster et al., "The Tα1 α-Tubulin Promoter Specifies Gene Expression as a Function of Neuronal Growth and Regeneration in Transgenic Mice," *J. Neurosci.* 14:7319-7330 (1994).
Godfraind et al., "In Vivo Analysis of Glial Cells Phenotypes During a Viral Demyelinating Disease in Mice," *J. Cell Biol.* 109:2405-2416 (1989).
Goldman and Windrem, "Cell Replacement Therapy in Neurological Disease," *Phil. Trans. R. Soc. B* 361:1463-1475 (2006).
Goldman and Windrem, "Stem Cell-Based Strategies for Treating Pediatric Disorders of Myelin," *Human Molecular Genetics* 17(10):R76-R83 (2008).
Goldman et al., "How to Make an Oligodendrocyte," *Development* 142:3983-3995 (2015).
Goldman et al., "Glial Progenitor Cell-Based Treatment and Modeling of Neurological Disease," *Science* 338:491-495 (2012).
Gout et al., "Remyelination by Transplanted Oligodendrocytes of a Demyelinated Lesion in the Spinal Cord of the Adult Shiverer Mouse," *Neurosci. Lett.* 87:195-199 (1988).
Gruber, "The Case for Local Immunosuppression," *Transplantation* 54:1-11 (1992).
Gumpel et al., "Myelination and Remyelination in the Central Nervous System by Transplanted Oligodendrocytes Using the Shiverer Model," *Dev. Neurosci.* 11:132-139 (1989).
Gutman et al., International Union of Pharmacology. XLI. Compendium of Voltage-Gated Ion Channels: Potassium Channels. *Pharmacol. Rev.* 55:583-586 (2003).
Hall et al., "Spinal Cord Oligodendrocytes Develop from Ventrally Derived Progenitor Cells that Express PDGF Alpha-Receptors," *Development* 122: 4085-4094 (1996).
Han et al., "Direct Reprogramming of Fibroblasts into Neural Stem Cells by Defined Factors," *Cell Stem Cell* 10:465-472 (2012).
Han et al., "Forebrain Engraftment by Human Glial Progenitor Cells Enhances Synaptic Plasticity and Learning in Adult Mice," *Cell Stem Cell* 12:342-353 (2013).
Hanna et al., "Direct Reprogramming of Terminally Differentiated Mature B Lymphocytes to Pluripotency," *Cell* 133(2):250-264 (2008).
Hatch et al., "Derivation of High-Purity Oligodendroglial Progenitors," *Methods in Molecular Biology* 549:59-74 (2009).
Holst et al., "Binding ans Activation of the Promoter for the Neural Cell Adhesion Molecule by Pax-8," *J. Biol. Chem.* 269:22245-22252 (1994).
http://www.pierce-antibodies.com/PDGF-RA-CD140a-antibody-Polyclonal--PA532545.html.
Hu et al., "Differentiation of Human Oligodendrocytes From Pluripotent Stem Cells," *Nat Protoc.* 4(11):1614-1622 (2009).
Hu et al., "Efficient Generation of Transgene-Free Induced Pluripotent Stem Cells from Normal and Neoplastic Bone Marrow and Cord Blood Mononuclear Cells," *Blood* doi:10.1182/blood-2010-07-298331 (Feb. 4, 2011).
Hu et al., "Neural Differentiation of Human Induced Pluripotent Stem Cells Follows Developmental Principles But With Variable Potency," *Proc. Nat. Acad. Sci. USA* 107(9):4335-4340 (2010).
Hu et al., "Human Oligodendrocytes From Embryonic Stem Cells: Conserved SHH Signaling Networks and Divergent FGF Effects," *Development* 136(9):1443-1452 (2009).
Huangfu et al., "Induction of Pluripotent Stem Cell from Primary Human Fibroblasts with Only Oct4 and Sox2," *Nat. Biotechnol.* 26:1269-1275 (2008).
International Search Report and Written Opinion for International Application No. PCT/US14/15019 (dated May 7, 2014).
International Preliminary Report on Patentability for International Application No. PCT/US14/15019 (dated Aug. 11, 2015).
International Preliminary Report on Patentability for International Application No. PCT/US2009/043140 (dated Nov. 9, 2010).
International Search Report for International Application No. PCT/US2009/043140 (dated Mar. 8, 2010).
Irizarry et al., "Exploration, Normalization, and Summaries of High Density Oligonucleotide Array Probe Level Data," *Biostatistics* 4(2):249-64 (2003).
Izrael et al., "Human Oligodendrocytes Derived From Embryonic Stem Cells: Effect of Noggin on Phenotypic Differentiation In Vitro and on Myelination In Vivo," *Mol Cell Neurosci.* 34(3):310-23 (2007).
Jang et al., "A Segment of the 5' Nontranslated Region of Encephalomyocarditis Virus RNA Directs Internal Entry of Ribosomes During In vitro Translation," *J. Virol.* 62:2636-2643 (1988).
Jeffery et al., "Behavioural Consequences of Oligodendrocyte Progenitor Cell Transplantation into Experimental Demyelinating Lesions in the Rat Spinal Cord," *Eur. J. Neurosci.* 11:1508-1514 (1999).
K.A. Nave, "Neurological Mouse Mutants and the Genes of Myelin," *J. Neurosci. Res.* 38(6):607-12 (1994).
Karschin et al., "IRK (1-3) and GIRK (1-4) Inwardly Rectifying $K^+$ Channel mRNAs are Differentially Expressed in the Adult Rat Brain," *J. Neurosci.* 16:3559-3570 (1996).

(56) References Cited

OTHER PUBLICATIONS

Keirstead et al., "Human Embryonic Stem Cell-Derived Oligodendrocyte Progenitor Cell Transplants Remyelinate and Restore Locomotion After Spinal Cord Injury," *J Neurosci.* 25(19):4694-705 (2005).
Kennea et al., "Neural Stem Cells," *Journal of Pathology* 197:536-550 (2002).
Keyoung et al., "High-Yield Selection and Extraction of Two Promoter-Defined Phenotypes of Neural Stem Cells from the Fetal Human Brain," *Nature Biotechnology* 19:843-50 (2001).
Kim et al., "Oct4-Induced Pluripotency in adult Neural Stem Cells,"*Cell* 136(3):411-419 (2009).
Kim et al., "Pluripotent Stem Cells Induced from Adult Neural Stem Cells by Reprogramming with Two Factors," *Nature* 454:646-650 (2008).
Kirschenbaum et al., "In vitro Neuronal Production and Differentiation by Precursor Cells Derived from the Adult Human Forebrain," *Cerebral Cortex* 4(6):576-89 (1994).
Klapstein et al., "Electrophysiological and Morphological Changes in Striatal Spiny Neurons in R6/2 Huntington's Disease Transgenic Mice," *J. Neurophysiol.* 86:2667-2677 (2001).
Kolf et al., "Biology of Adult Mesenchymal Stem Cells: Regulation of Niche, Self-Renewal and Differentiation," *Arthritis Research & Therapy* 9(204):204-213 (2007).
Krebs et al., "The JC Virus Minimal Core Promoter is Glial Cell Specific in Vivo," *J. Virol.* 69:2434-42 (1995).
Lachapelle et al., "Transplantation of CNS Fragments into the Brain of Shiverer Mutant Mice: Extensive Myelination by Implanted Oligodendrocytes," *Dev. Neurosci.* 6:325-334 (1983).
Larochelle et al., "Inhibition of Platelet-Derived Growth Factor Autocrine Growth Stimulation by a Monoclonal Antibody to the Human Alpha Platelet-Derived Growth Factor Receptor," *Cell Growth Differ.* 4(7):547-53 (1993).
Larsen et al., "Contributions of the Na(+)/K(+)-ATPase, NKCC1, and Kir4.1 to Hippocampal K(+) Clearance and Volume Responses," *Glia* 62(4):608-622 (2014).
Laszkiewicz et al., "Structural Characterization of Myelin-associated Glycoprotein Gene Core Promoter," *J. Neurosci. Res.* 50(6):928-36 (1997).
Learish et al., "Intraventricular Transplantation of Oligodendrocyte Progenitors into a Fetal Myelin Mutant Results in Widespread Formation of Myelin," *Annals of Neurology* 46(5):716-722 (1999).
Lesage et al., "Cloning Provides Evidence for a Family of Inward Rectifier and G-Protein-Coupled K+ Channels in the Brain," *FEBS Lett* 353:37-42 (1994).
Li et al., "Oligodendrocyte Progenitor Cells in the Adult Rat CNS Express Myelin Oligodendrocyte Glycoprotein (MOG)," *Brain Pathol.* 12(4):463-471 (2002).
Liu et al., "CD44 Expression Identifies Astrocyte-Restricted Precursor Cells," *Dev. Biol.* 276:31-46 (2004).
Liu et al., "Isolation and Sequencing of the 5' end of the Rat Microtubule-Associated Protein (MAP1B)-Encoding cDNA," *Gene* 171:307-308 (1996).
Linner et al., "A New Technique for Removal of Amorphous Phase Tissue Water Without Ice Crystal Damage: A Preparative Method for Ultrastructural Analysis and Immunoelectron Microscopy," *J. Histochem. Cytochem.* 34(9):1123-35 (1986).
Lobsiger et al., "Glial Cells as Intrinsic Components of Non-Cell-Autonomous Neurodegenerative Disease," *Nature Neurosci.* 10(11):1355-1360 (2007).
Mangiarini et al., "Exon 1 of the HD Gene with an Expanded CAG Repeat is Sufficient to Cause a Progressive Neurological Phenotype in Transgenic Mice," *Cell* 87:493-506 (1996).
Matsui et al., "Independent Expression of Human α or β Platelet-Derived Growth Factor Receptor cDNAs in a Naïve Hematopoietic Cell Leads to Functional Coupling with Mitogenic and Chemotactic Signaling Pathways," *Proc. Natl. Acad. Sci. USA* 86:8314-8318 (1989).
Mazur, "The Role of Intracellular Freezing in the Death of Cells Cooled at Supraoptimal Rates," *Cryobiology* 14:251-272(1977).

Mehler et al., "Progenitor Cell Biology: Implications for Neural Regeneration," *Archives of Neurology* 56(7):780-784 (1999).
Meissner et al. "Direct Reprogramming of Genetically Unmodified Fibroblasts into Pluripotent Stem Cells," *Nat. Biotech.* 25:1177-1181 (2007).
Mermelstein et al., "Inwardly Rectifying Potassium (IRK) Currents are Correlated with IRK Subunit Expression in Rat Nucleus Accumbens Medium Spiny Neurons," *J. Neurosci.* 18:6650-6661 (1998).
Meyer et al., "Direct Conversion of Patient Fibroblasts Demonstrates Non-Cell Autonomous Toxicity of Astrocytes to Motor Neurons in Familial and Sporadic ALS," *Proc Natl Acad Sci USA.* 111(2): 829-832 (2014).
Milward et al., "Isolation and Transplantation of Multipotential Populations of Epidermal Growth Factor-Responsive, Neural Progenitor Cells from the Canine Brain," *Journal of Neuroscience Research* 50:862-871 (1997).
Munson et al. "Ligand: A Versatile Computerized Approach for Characterization of Ligand-Binding Systems," *Anal. Biochem.* 107:220-239 (1980).
Narsinh et al., "Comparison of Human Induced Pluripotent and Embryonic Stem Cells: Fraternal or Identical Twins?," *Molecular Therapy* 19(4):635-638 (2011).
Nisenbaum et al., "Isolation and Characterization of a Persistent Potassium Current in Neostriatal Neurons," *J. Neurophysiol.* 76:1180-1194 (1996).
Nisenbaum et al., "Potassium Currents Responsible for Inward and Outward Rectification in Rat Neostriatal Spiny Projection Neurons," *J. Neurosci.* 15:4449-4446.
Notice of Reasons for Rejections for JP 2015-557053 (dated Dec. 4, 2017).
Nunes et al., "Identification and Isolation of Multipotential Neural Progenitor Cells from the Subcortical white Matter of the Adult Human Brain," *Nat. Med.* 9(4):439-447 (2003).
Oberheim et al., "Astrocytic Complexity Distinguishes the Human Brain," *Trends in Neurosci.* 29(10): 1-10 (2006).
Oberheim et al., "Uniquely Hominid Features of Adult Human Astrocytes," *J. Neurosci.* 29(10): 3276-3287 (2009).
Office Action in U.S. Appl. No. 14/764,507 (dated Dec. 22, 2016).
Office Action in U.S. Appl. No. 14/764,507 (dated Aug. 2, 2017).
Office Action in U.S. Appl. No. 14/764,507 (dated Jul. 10, 2018).
Office Action in U.S. Appl. No. 15/427,986 (dated Apr. 18, 2018).
Office Action for Canadian Patent Application No. 2,723,382, 4 pages (dated May 27, 2015).
Office Action in U.S. Appl. No. 12/990,874 (dated Nov. 10, 2016).
Office Action in U.S. Appl. No. 12/990,874 (dated May 4, 2016).
Office Action in U.S. Appl. No. 12/990,874 (dated Oct. 20, 2015).
Office Action in U.S. Appl. No. 12/990,874 (dated May 14, 2014).
Office Action in U.S. Appl. No. 12/990,874 (dated Mar. 15, 2013).
Okita. et al., "Generation of Germline-Competent Induced Pluripotent Stem Cells," *Nature* 448:313-317 (2007).
Park et al. "Reprogramming of Human Somatic Cells to Pluripotency with Defined Factors," *Nature* 451:141-146 (2008).
Park et al., "Analysis of Upstream Elements in the HuC Promoter Leads to the Establishment of Transgenic Zebrafish with Fluorescent Neurons," *Dev. Biol.* 227(2): 279-293 (2000).
PE anti-human CD140a (PDGFRalpha) antibody http://www.biolegend.com/.
Pouya et al., "Human Induced Pluripotent Stem Cells Differentiation into Oligodendrocyte Progenitors and Transplantation in a Rat Model of Optic Chiasm Demyelination," *PLos ONE* 6(11):e27925 (2011).
Pringle et al., "PDGF Receptors in the Rat CNS: During Late Neurogenesis, PDGF Alpha-Receptor Expression Appears to be Restricted to Glial Cells of the Oligodendrocyte Lineage," *Development* 115:535-551 (1992).
Rasband et al., "Developmental Clustering of Ion Channels at and Near the Node of Ranvier," *Dev. Biol.* 236(1):5-16 (2001).
Rao et al., "Conserved and Divergent Paths that Regulate Self-Renewal in Mouse and Human Embryonic Stem Cells," *Developmental Biology* 275:269-286 (2004).
Readhead et al., "Expression of a Myelin Basic Protein Gene in Transgenic Shiverer Mice: Correction of the Dysmyelinating Phenotype," *Cell* 48:703-712 (1987).

(56) References Cited

OTHER PUBLICATIONS

Reitz et al., "Alzheimer Disease: Epidemiology, Diagnostic Criteria, Risk Factors and Biomarkers," *Biochem. Pharmacol.* 88(4):640-651 (2014).
Rossi et al., "Neural Stem Cell Therapy for Neurological Diseases: Dreams and Reality," *Nature Reviews Neuroscience* 3:401-409 (2002).
Roy et al., "In vitro Neurogenesis by Progenitor Cells Isolated from the Adult Human Hippocampus," *Nature Med.* 6:271-277 (2000).
Roy et al., "Identification, Isolation, and Promoter-Defined Separation of Mitotic Oligodendrocyte Progenitor Cells from the Adult Human Subcortical White Matter," *J. Neurosci.* 19(22):9986-9995 (1999).
Roy et al., "Telomerase-immortalization of neuronally restricted progenitor cells derived from the human fetal spinal cord," *Nature Biotechnol.* 22:297-305 (2004).
Schafer et al., "Glial Regulation of the Axonal Membrane at Nodes of Ranvier," *Curr. Opinion in Neurobiology* 16:508-514 (2006).
Scherer et al., "Differential Regulation of the 2',3'-Cyclic Nucleotide 3'-Phosphodiesterase Gene During Oligodendrocyte Development" *Neuron* 12:1363-75 (1994).
Schultz et al., "NOD/LtSz-Rag1$^{null}$Pfp$^{null}$ Mice: A New Model System with Increased Levels of Human Peripheral Leukocyte and Hematopoietic Stem-Cell Engraftment," *Transplantation* 76:1036-1042 (2003).
Scolding et al., "Identification of A2B5-Positive Putative Oligodendrocyte Progenitor Cells and A2B5-Positive Astrocytes in Adult Human White Matter," *Neurosci.* 89(1):1-4 (1999).
Scoulding et al., "Oligodendrocyte Progenitors are Present in the Normal Adult Human CNS and in the Lesions of Multiple Sclerosis," *Brain* 121:2221-2228 (1998).
Sherman et al., "Mechanisms of Axon Ensheathment and Myelin Growth," *Nature Rev. Neurosci.* 6:683-690 (2005).
Seilhean et al., "Myelination by Transplanted Human and Mouse Central Nervous System Tissue After Long-Term Cryopreservation," *Acta Neuropathologica* 91(1):82-88 (1989).
Shin et al., "Expression of Mutant Huntingtin in Glial Cells Contributes to Neuronal Excitotoxicity," *J. Cell. Biol.* 171(6):1001-1012 (2005).
Shinkai et al., "RAG-2 Deficient Mice Lack Mature Lymphocytes Owing to Inability to Initiate V(D)J Rearrangement," *Cell* 68(5): 855-67 (1992).
Sim et al., "CD140a Identifies a Population of Highly Myelinogenic, Migration-Competent, and Efficiently Engrafting Human Oligodendrocytes Progenitor Cells," *Nature Biotechnol.* 29(10):934-941 (2011).
Sim et al., "Complementary Patterns of Gene Expression by Human Oligodendrocyte Progenitors and their Environment Predict Determinants of Progenitor Maintenance and Differentiation," *Ann. Neurol.* 59(5):763-79 (2006).
Sim et al., "Fate Determination of Adult Human Glial Progenitor Cells," *Neuron Glia Biol.* 5(3/4):45-55 (2009).
Smyth, "Linear Models and Empirical Bayes Methods for Assessing Differential Expression in Microarray Experiments," *Stat. Appl. Genet. Mol. Bio.* 3:Article 3 (2004).
Smithies et al. "Insertion of DNA Sequences Into the Human Chromosomal β-Globin Locus by Homologous Recombination," *Nature* 317:230-234 (1985).
Sommer and Mostoslavsky, "Experimental Approaches for the Generation of Induced Pluripotent Stem Cells," *Stem Cell Res. Ther.* 1:26 doi:10.1186/scrt26 (Aug. 10, 2010).
Sommer et al., "Generation of Human Induced Pluripotent Stem Cells from Peripheral Blood using the STEMCCA Lentiviral Vector," *J. Vis. Exp.* 68:e4327 doi:10.3791/4327 (2012).
Song et al., "Somatodendritic Depolarization-Activated Potassium Currents in Rat Neostriatal Cholinergic Interneurons are Predominantly of the A Type and Attributable to Coexpression of Kv4.2 and Kv4.1 Subunits," *J. Neurosci.* 18(9):3124-37 (1998).
Sorge et al., "Olfactory Exposure to Males, Including Men, Causes Stress and Related Analgesia in Rodents,". *Nature Methods* 11: 629-632 (2014).
Southwell et al., "A Fully Humanized Transgenic Mouse Model of Huntington Disease," *Human Molecular Genetics* 22(1):18-34 (2013).
Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi:10.1093/eurheartj/ehs203 (2012).
Surmeier et al., "Developmental Regulation of a Slowly Inactivating Potassium Conductance in Rat Neostriatal Neurons," *Neurosci. Lett.* 122:41-46 (1991).
Sullivan et al., "Induced Pluripotent Stem Cells: Epigenetic Memories and Practical Implications," *Mol. Hum. Reprod.* 16(12);880-5 (2010).
Summons to Attend Oral Proceedings for European Patent Application No. 09743660.4, 5 pages. (Sep. 28, 2015).
Supplementary Search Report and Search Opinion for EP14749594.9 dated Jun. 20, 2016.
Takahashi et al., "Induction of Pluripotent Stem Cells from Mouse Embryonic and Adult Fibroblast Cultures by Defined Factors," *Cell*, 126(4):663-676 (2006).
Takahashi et al., "Induction of Pluripotent Stem Cells from Adult Human Fibroblasts by Defined Factors," *Cell* 131:861-872 (2007).
Talan J., "Human Glial Progenitor Cells Remyelinate in Shiverer Mouse: Plans to Study Cell Grafts in Children with Myelin Disease," *Neurology Today* 8(14):1 (2008).
Terada et al., "The Tetraspanin Protein, CD9, Is Expressed by Progenitor Cells Committed to Oligodendrogenesis and Is Linked to B1 Integrin, CD81, and Tspan-2," *GLIA* 40:350-359 (2002).
Tkatch et al., "Kv4.2 mRNA Abundance and A-Type K($^+$) Current Amplitude are Linearly Related in Basal Ganglia and Basal Forebrain Neurons," *J. Neurosci.* 20(2):579-88 (2000).
Tong et al., "Astrocyte Kir4.1 Ion Channel Deficits Contribute to Neuronal Dysfunction in Huntington's Disease Model Mice," *Nat. Neurosci.* 17:694-703 (2014).
Totonchi et al., "Feeder- and serum-free establishment and expansion of human induced pluripotent stem cells," *Int. J. Dev. Biol.* 54:877-886 (2010).
Tyszka et al., "Statistical Diffusions Tensor Histology Reveals Regional Dysmyelination Effects in the Shiverer Mouse Mutant," *NeuroImage* 29(4):1058-65 (2006).
UniProt, UniProtKB—P16234 (PDGFRA_Human), available at http://www.uniprot.org/uniprot/P16234, accessed Jan. 20, 2016.
Vaskova et al., "Epigenetic Memory" Phenomenon in Induced Pluripotent Stem Cells, *Acta Naturae* 5(4):15-21 (2013).
Walker F., "Huntington's Disease," *Lancet* 369:218-228 (2007).
Wang et al., "Isolation of Neuronal Precursors by Sorting Embryonic Forebrain Transfected with GFP Regulated by the Tα1 Tubulin Promoter," *Nature Biotechnology* 16:196-201 (1998).
Wang et al., "Human iPSC-Derived Oligodendrocyte Progenitor Cells Can Myelinate and Rescue a Mouse Model of Congenital Hypomyelination," *Cell Stem Cell* 12:252-264 (2013).
Wang et al, "Induction of Immune Tolerance in Mice with a Novel Mucosal Nanoemulsion Adjuvant and Self-Antigen," *Nanomedicine* 7(6):867-76 (2012).
Wang et al., "Astrocytes Modulate Neural Network Activity by Ca(2)+-Dependent Uptake of Extracellular K$^+$," *Sci Signal.* 5(218): ra26 (2012).
Wang et al., "Bergmann Glia Modulate Cerebellar Purkinje Cell Bistability via Ca$^{2+}$-Dependent K$^+$ Uptake," *Proc Natl Acad Sci USA* 109(20):7911-6 (2012).
Wang et al., "Prospective Identification, Direct Isolation, and Expression Profiling of a Telomerase Expressing Subpopulation of Human Neural Stem Cells, Using Sox2 Enhancer-Directed FACS," J. Neurosci. 30:14635-14648 (2010).
Waters et al., "Huntington Disease Skeletal Muscle is Hyperexcitable Owing to Chloride and Potassium Channel Dysfunction," *Proc Natl Acad Sci USA*. 110(22): 9160-9165 (2013).
Wight et al., "Regulation of Murine Myelin Proteolipid Protein Gene Expression," *J. Neurosci. Res.* 50(6): 917-27 (1997).

(56) References Cited

OTHER PUBLICATIONS

Wilson et al., "The Origins of Two-State Spontaneous Membrane Potential Fluctuations of Neostriatal Spiny Neurons," *J. Neurosci.* 16(7):2397-410 (1996).
Windrem et al., "A Competitive Advantage by Neonatally Engrafted Human Glial Progenitors Yields Mice whose Brains are Chimeric for Human Glia," *J. Neurosci.* 34(48):16153-16161 (2014).
Windrem et al., "Fetal and Adult Human Oligodendrocyte Progenitor Cell Isolates Myelinate the Congenitally Dysmyelinated Brain," Nature Medicine 10:93-97 (2004).
Windrem et al., "Neonatal Chimerization with Human Glial Progenitor Cells Can Both Remyelinate and Rescue the Otherwise Lethally Hypomyelinated Shiverer Mouse," *Cell* 2:553-65 (2008).
Windrem et al., "Progenitor Cells Derived from the Adult Human Subcortical White Matter Disperse and Differentiate as Oligodendrocytes Within Demyelinated Lesions of the Rat Brain," *J. Neurosci. Res.* 69:966-975 (2002).
Written Opinion for corresponding International Application No. PCT/US2009/043140, 6 pages (dated Mar. 8, 2010).
Yamanaka et al., "Astrocytes as Determinants of Disease Progression in Inherited Amyotrophic Lateral Sclerosis," Nat. Neurosci. 11(3):251-253 (2008).
Yang et al., "A Novel Approach for Amplification and Purification of Mouse Oligodendrocyte Progenitor Cells," *Frontiers in Cellular Neuroscience* 10:article 203, p. 1-10 (2016).
Yang et al., "βIV Spectrin is Recruited to Axon Initial Segments and Nodes of Ranvier by AnkyrinG," *J. Cell Biol* 176:509-519 (2007).
Yu et al. "Induced Pluripotent Stem Cell Lines Derived from Human Somatic Cells." *Science* 318(5858):1917-20 (2007).
Zennou et al., "The HIV-1 DNA Flap Stimulates HIV Vector-Mediated Cell Transduction in the Brain," *Nat Biotechnol* 19: 446-450 (2001).
Zhao et al., "Two Supporting Factors Greatly Improve the Efficiency of Human iPSC Generation," *Cell Stem Cell* 3:475-479 (2008).
Zufferey et al., "Self-Inactivating Lentivirus Vector for Safe and Efficient in vivo Gene Delivery," *J. Virol.* 72:9873-9880 (1998).
Zufferey et al., "Woodchuck Hepatitis Vims Posttranscriptional Regulatory Element Enhances Expression of Transgenes Delivered by Retroviral Vectors," *J. Virol.* 73:2886-2892 (1999).
Giampa et al., "Systemic Delivery of Recombinant Brain Derived Neurotrophic Factor (BDNF) in the R6/2 Mouse Model of Huntington's Disease," PLoS One 8(5):e64037 (2013).
Office Action for U.S. Appl. No. 15/429,559 (dated Sep. 28, 2018).
Yandava et al., "'Global' Cell Replacement is Feasible via Neural Stem Cell Transplantation: Evidence from the Dysmyelinated Shiverer Mouse Brain," Proc. Natl. Acad. Sci. USA 96:7029-7034 (1999).
Warrington et al., "Differential Myelinogenic Capacity of Specific Developmental Stages of the Oligodendrocyte Lineage Upon Transplantation Into Hypomyelinating Hosts," J. Neurosci. Res.34:1-13 (1993).
Gumpel et al., "Transplantation of Human Embryonic Oligodendrocytes into Shiverer Brain," Ann. NY Acad. Sci. 495:71-85 (1987).
Lokker et al., "Functional Importance of Platelet-derived Growth Factor (PDGF) Receptor Extracellular Immunoglobulin-like Domains," J. Biol. Chem. 272(52):33037-44 (1997).
Search result of PDGFRA at The Human Protein Atlas (www.Proteinatlas.org).

\* cited by examiner

NON-HUMAN MAMMAL MODEL OF HUMAN DEGENERATIVE DISORDER, USES THEREOF, AND METHOD OF TREATING HUMAN DEGENERATIVE DISORDER

This application is a division of U.S. patent application Ser. No. 14/701,245, filed Apr. 30, 2015, which is hereby incorporated by reference in its entirety.

This invention was made with government support under R01MH099578 and R01NS75345awarded by the National Institutes of Health. The government has certain rights in the invention.

FIELD

The present application relates to a non-human mammal model of a human neurodegenerative disorder, uses thereof, and methods of treating human degenerative disorders.

BACKGROUND

Glial form and function are extraordinarily divergent with evolution, and human astrocytes are virtually unique in their pleomorphism and fiber complexity. In particular, human astrocytes are larger and more structurally complex than rodent glia, and coordinate the actions of vastly more synapses within their geographic domains. Engrafting neonatal mice with human glial progenitor cells ("hGPCs") to establish brains chimeric for human astrocytes has permitted assessment of the relative contributions of glial cells to the species-specific aspects of human cognition. These human glial chimeric mice exhibit substantially enhanced activity-dependent plasticity and learning establishing the potential of their use to assess human-specific aspects of the contributions of astrocytes to cognition (Han et al., "Forebrain Engraftment by Human Glial Progenitor Cells Enhances Synaptic Plasticity and Learning in Adult Mice," *Cell Stem Cell* 12: 342-353 (2013)).

Astrocytic involvement in human cognitive disorders has never been studied, and yet its role may be profound. As a case in point, a number of conditions, especially several neuropsychiatric disorders, are specific to humans. Yet while human neuronal cytoarchitecture is not very different from that of primates, astrocytic pleomorphism exhibits a quantal leap with human evolution, concurrent with the appearance of a number of neuropsychiatric, neurodevelopmental, and neurodegenerative conditions that appear unique to humans. In particular, glial pathology has been noted to contribute to a broad set of neuropsychiatric and neurodegenerative diseases traditionally considered disorders of solely neuronal dysfunction (Di Giorgio et al., "Human Embryonic Stem Cell-Derived Motor Neurons are Sensitive to the Toxic Effect of Glial Cells Carrying an ALS-Causing Mutation," *Cell Stem Cell* 3 (6): 637-648 (2008); Di Giorgio et al., "Non-Cell Autonomous Effect of Glia on Motor Neurons in an Embryonic Stem Cell-Based ALS Model," *Nat. Neurosci.* 10 (5):608-614 (2007); Verkhratsky et al., Astrogliopathology in Neurological, Neurodevelopmental and Psychiatric Disorders," *Neurobiol Dis*. pii: S0969-9961 (15) 00103-5 (2015); Meyer et al., "Direct Conversion of Patient Fibroblasts Demonstrates Non-Cell Autonomous Toxicity of Astrocytes to Motor Neurons in Familial and Sporadic ALS," *Proc Natl Acad Sci USA*. 111 (2): 829-832 (2014); and Yamanaka et al., "Astrocytes as Determinants of Disease Progression in Inherited Amyotrophic Lateral Sclerosis," *Nat Neurosci*. 11 (3): 251-253 (2008)).

Huntington's disease ("HD") is a prototypic neurodegenerative disorder, characterized by abnormally long CAG repeat expansions in the first exon of the Huntingtin gene. The encoded polyglutamine expansions of mutant huntingtin protein disrupt its normal functions and protein-protein interactions, ultimately yielding widespread neuropathology, most rapidly evident in the neostriatum. Yet despite the pronounced loss of medium spiny neurons ("MSNs") of the neostriatum in HD, and evidence of glial dysfunction (Tong et al., "Astrocyte Kir4.1 Ion Channel Deficits Contribute to Neuronal Dysfunction in Huntington's Disease Model Mice," *Nat. Neurosci.* 17:694-703 (2014) and Shin et al., "Expression of Mutant Huntingtin in Glial Cells Contributes to Neuronal Excitotoxicity," *J Cell Biol.* 171:1001-1012 (2005)), few studies have investigated the specific contribution of glial pathology either to striatal neuronal dysfunction in HD, or more broadly, to disease phenotype. The lack of understanding of the role of glial pathology in HD has reflected the lack of in vivo models that permit the separate interrogation of glial and neuronal functions in HD, particularly so in humans. Indeed, this gap in knowledge is especially concerning in light of the marked differences between human and rodent glia; human astrocytes are larger and more structurally complex than rodent glia, and coordinate the actions of vastly more synapses within their geographic domains (Oberheim et al., "Uniquely Hominid Features of Adult Human Astrocytes," *J. Neurosci.* 29 (10): 3276-3287 (2009) and Oberheim et al., "Astrocytic Complexity Distinguishes the Human Brain," *Trends in Neurosci*. 29 (10): 1-10 (2006)). Accordingly, mice neonatally engrafted with astrocyte-biased hGPCs, which develop brains chimeric for human astroglia and their progenitors (Windrem et al., "A Competitive Advantage by Neonatally Engrafted Human Glial Progenitors Yields Mice whose Brains are Chimeric for Human Glia," *J. Neurosci*. 34 (48): 16153-16161 (2014)), exhibit substantially enhanced activity-dependent plasticity and learning (Han et al., "Forebrain Engraftment by Human Glial Progenitor Cells Enhances Synaptic Plasticity and Learning in Adult Mice," *Cell Stem Cell* 12 (3): 342-353 (2013)). Yet this relatively greater role of human astrocytes in neural processing suggests the potential for glial pathology to wreck especial havoc within human neural circuits, with attendant implications for the human neurodegenerative disorders.

The present invention is directed to overcoming these and other deficiencies in the art.

SUMMARY

A first aspect of the present disclosure relates to a non-human mammal model of a human neurodegenerative disorder, wherein at least 30% of all of the glial cells in its corpus callosum are human glial cells and/or at least 5% of all of the glial cells in the white matter of its brain and/or brain stem are human neurodegenerative disorder specific glial cells.

Another aspect of the present disclosure relates to a method of identifying an agent suitable for treating a neurodegenerative disorder. This method involves providing a non-human mammal model of a neurodegenerative disorder with at least 30% of the glial cells in its corpus callosum being human glial cells and/or at least 5% of the glial cells in its brain and brain stem white matter being human neurodegenerative disorder specific glial cells. This method further involves providing a candidate agent; administering the candidate agent to the non-human mammal; and assessing, as a result of said administering, the therapeutic potential of said candidate agent as suitable for treating the neurodegenerative disorder.

Another aspect of the present disclosure relates to a method of producing a non-human mammal model of a human neurodegenerative disorder. This method involves providing a population of isolated human neurodegenerative disorder specific glial cells; introducing the population of isolated human neurodegenerative disorder specific glial cells into multiple locations within the forebrain and/or brain stem of the non-human mammal; and recovering the non-human mammal with human neurodegenerative disorder specific glial cells replacing native glial cells in the brain.

Another aspect of the present disclosure relates to a method of treating a neurodegenerative disorder selected from the group consisting of: Huntington's disease, Alzheimer's disease, frontotemporal dementia, and amyotrophic lateral sclerosis in a subject. This method involves selecting a subject having the neurodegenerative disorder and administering to the selected subject a preparation of glial progenitor cells at a dosage effective to treat the neurodegenerative disorder in the subject.

A fifth aspect relates to a method of restoring normal brain interstitial $K^+$ levels in a subject with dysregulated glial $K^+$ channel function. This method involves selecting a subject having dysregulated glial $K^+$ channel function and administering to the selected subject a preparation of glial progenitor cells at a dosage effective to restore normal brain interstitial glial $K^+$ levels in the selected subject.

The contribution of glial pathology to neurodegenerative disorders (i.e., Huntington's disease, Alzheimer's disease, frontotemporal dementia, and amyotrophic lateral sclerosis) is poorly understood. Applicants have established human HD glial chimeric mice by neonatally engrafting the striata of immunodeficient mice with mutant huntingtin ("mHtt")-expressing hGPCs, derived from either huntingtin mutant human embryonic stem cells ("hESCs") or mHTT-transduced human striatal neural stem cells. As described herein, mice engrafted with mHTT-expressing (48Q) hESC GPCs exhibited significantly worse motor performance than controls chimerized with normal (18Q) hESC GPCs. To assess the basis for this effect, human glial chimeras were established using human fetal striatal GPCs transduced to express the first exon of mutant HTT (73 Q and 23Q), and patch clamped local MSNs. As described herein, medium spiny neurons in the mHTT glial environment manifested higher input resistance, less frequent spontaneous excitatory post synaptic potentials ("EPSPs"), and lower excitation thresholds than those resident with normal (23Q) HTT-transduced glia. Applicants also investigated whether the converse manipulation (i.e. engraftment with normal glia into a Huntington's disease environment) might slow disease progression in R6/2 (120Q) HD mice. As described herein, R6/2 mice engrafted with normal hGPCs survived longer than unengrafted R6/2s, and manifested slower motor deterioration, while their MSNs exhibited lower input resistance, more frequent spontaneous EPSPs, and were less excitable. Furthermore, whereas R6/2 mice exhibited abnormally high levels of interstitial potassium, chimerization with normal glial restored striatal potassium levels to near normal. These observations suggest a causal role for glia in HD, and indicate that the colonization of diseased striata with healthy glia may slow disease progression.

BRIEF DESCRIPTION OF THE DRAWINGS

FIG. 1A shows that mice engrafted with hESC GPCs expressing either normal Htt (GENEA19; 18Q) or mutant Htt (GENEA20, 48Q; a sibling to GENEA19) manifested striatal chimerization by 20 weeks of age, which was denser at 40 weeks. FIG. 1A also shows that mice engrafted with GENEA20-derived glia (48Q) manifested striatal chimerization analogous to that of GENEA19-derived normal HTT (18Q) glia. FIG. 1B illustrates GENEA 19-derived glia identified by their expression of the human-specific nuclear antigen hNA interspersed with host cells (DAPI), revealing extent of striatal and cortical human glial chimerization at 40 weeks. FIGS. 1C and 1D show GENEA19 hGPC-engrafted striatal sections at 20 weeks (FIG. 1C) and 40 weeks (FIG. 1D) post-graft, stained for human and mouse NG2, showing the progressive domination of the striata by human NG2-defined GPCs. FIGS. 1E-1F show 20 week (FIG. 1E) and 40 week (FIG. 1F) post-graft striata, stained for hNA and human PDGFRα, similarly showing the progressive domination of the striata by human GPCs. FIGS. 1G-1H show GENEA19 hGPC-engrafted striata at 20 weeks (FIG. 1G) or 40 weeks (FIG. 1H) weeks, stained for human GFAP and hNA, showing the maturation and age-dependent increase in fiber complexity of human astroglia in the host striatum. Scale: A-B: 1 mm; C-G: 50 μm; 25 μm.

FIG. 3A is an example of a host striatal neuron, filled with Alexa-594 after recording, surrounded by EGFP-tagged donor-derived glia. FIG. 3B shows representative action potentials recorded in response to current injection in host neurons in striata chimerized with 23Q mHTT- and 73Q mHTT-expressing hGPCs. FIG. 3C shows the striatal neurons of mice engrafted with 73Q mHTT human glia required significantly fewer current injections to achieve voltage thresholds for firing, than did those engrafted with 23Q mHTT-transduced or either EGFP-only transduced or untreated control glia. FIG. 3D-3F show the higher input resistance of striatal neurons in 73Q glial chimeras relative to both 23Q and GFP control glia-engrafted mice (FIG. 3D). Also shown are the current-voltage (FIG. 3E) and current-resistance (FIG. 3F) curves. FIG. 3G shows representative traces of spontaneous EPSCs from recorded neurons. FIG. 3H shows that despite their relative hyperexcitability, striatal neurons within 73Q glial chimeric striata manifested a significantly lower frequency of spontaneous EPSPs than did striatal neurons in all control groups. Scale: 50 μm.

FIGS. 4A-4B illustrate that fetal derived cells expanded to colonize the striata and ventral forebrain of engrafted mice by 20 weeks. FIG. 4C show that donor-derived cells in the striata of transplanted mice increased as a function of time. FIGS. 4D-4G show that by 20 weeks after neonatal graft, the donor hGPCs (human nuclear antigen) integrated as astrocytes (FIG. 4D; GFAP) or persisted as GPCs (FIGS. 4E-4F; PDGFαR and olig2), but did not give rise to neurons; no overlap was ever seen of hNA and NeuN expression (FIG. 4G; NeuN). FIG. 4H shows that resident human glia did not manifest detectable nuclear Htt aggregates, as assessed by EM48 immunostaining; the staining patterns of host Htt and donor human nuclear antigen were always entirely non-overlapping. Scale: FIGS. 4A-4B: 1 mm; FIGS. 4D-4H: 25 µm.

FIG. 5A shows that linear regression revealed that the rate of rotarod-assessed motor deterioration of R6/2 mice was significantly slower in mice engrafted with human GPCs than in untreated mice (F [3,608]=41.87; p<0.001). FIG. 5B shows that R6/2 (120Q)×rag1$^{-/-}$ mice whose striata were engrafted with human GPCs survived significantly longer than unengrafted mice, (n=29 hGPC-engrafted; n=28 untreated; p<0.01 by Mantel-Cox Log-rank test).

FIG. 6A is representative of whole-cell I-clamp recordings from rag1$^{-/-}$ wild-type ("WT-untreated"), CD44 hGPC-engrafted rag1$^{-/-}$ wild-types ("WT-hGPC"), R6/2×rag1$^{-/-}$ mice ("R6/2"), and CD44-engrafted rag1$^{-/-}$ R6/2 mice ("R6/2-hGPC"). Lines below each group of traces indicate the current injection steps. FIG. 6B shows that the input resistance $R_{input}$, was significantly higher in R6/2×rag1$^{-/-}$ striatal neurons than in wild-type×rag1$^{-/-}$ controls, but was partially restored to normal in R6/2 mice chimerized with normal CD44-sorted hGPCs. FIG. 6C shows representative traces of spontaneous EPSCs ("sEPSC") from striatal neurons recorded in rag1$^{-/-}$ control, CD44-engrafted R6/2×rag1$^{-/-}$, and CD44-engrafted R6/2×rag1$^{-/-}$ mice. FIGS. 6D-6F show the frequency (FIG. 6D), amplitude (FIG. 6E), and cumulative distribution (FIG. 6F) of sEPSCs. In FIG. 6D, the spontaneous EPSP frequency was significantly lower in R6/2 striatal neurons than in wild-type rag1$^{-/-}$ controls, but was restored in CD44-engrafted R6/2s to levels not significantly different from control. In contrast, the EPSP amplitude of R/2 striatal neurons was unaffected by chimerization (FIG. 6E). The lower frequency of sEPSPs in the R6/2 MSNs, and partial restoration by hGPC engraftment, was consistent across EPSP amplitudes. *, , and *, p<0.05, 0.01, and 0.001, by 1-way ANOVA with post hoc t tests (FIG. 6F).

FIGS. 8A-8C are images of glia derived from Q73 mHtt-transduced hGPCs developed inclusions. FIG. 8A shows astroglia derived from hGPCs; no Htt immunostaining is detectable in untreated cells. FIG. 8B shows that Q23 Htt-transduced cells overexpress cytoplasmic Htt bearing Q23 (23 CAG repeats in exon 1 of HTT), no inclusions are noted. FIG. 8C shows that Q73 mHtt-expressing astroglia express both high levels of Htt, and discrete cytosolic inclusions of mutant Htt protein. Histological analysis of FIGS. 8D-8E reveals dense engraftment by human donor cells, in both the Q23 (FIG. 8D) and Q73 (FIG. 8E) mHtt glial-engrafted chimeric striata, whose extents and distributions of human nuclear antigen ("hNA")-expressing donor cells were indistinguishable at the 12 week time-point at which electrophysiological recordings were obtained. FIG. 8F shows that donor-derived glia transduced to express Q73 mHtt (which express EGFP, following lenti-mHtt (exon1)-EGFP transduction) develop cytosolic inclusions (arrows) in vivo as well as in vitro. 12 weeks post-neonatal graft. FIGS. 8A-8C, 50 µm; FIGS. 8D-8E, 100 µm; FIG. 8F, 50 µm.

FIG. 9A is a schematic illustration of the major steps involved in isolating and culturing CD44-defined astrocyte-biased hGPCs, prior to their transplantation into neonatal mice. FIG. 9B shows the appearance of the CD44-sorted cells after isolation. FIG. 9C shows that the cells include a mix of GFAP+/olig2– astrocytes and GFAP+/olig2+ hGPCs. FIGS. 9D-9E show that cells were then grown to confluency and passaged (FIG. 9D), then cultured on ultralow attachment dishes for 2-5 days, in which they formed clusters of 50-100 µm diameter; these were spun and collected for transplant (FIG. 9E). Scale: 100 µm.

DETAILED DESCRIPTION

Figures 1A, 1B, 1C, 1D, 1E, 1F, 1G, 1H:
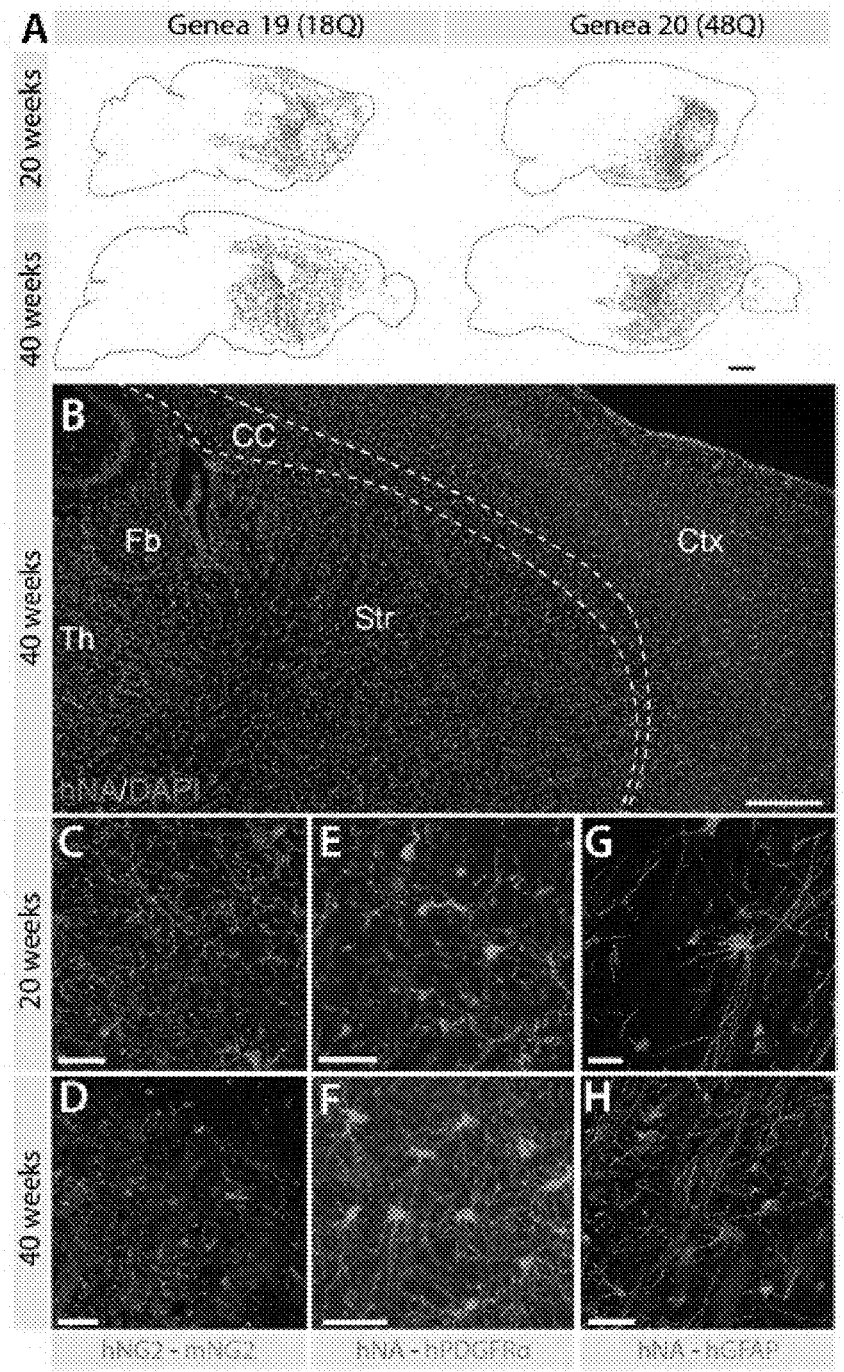
FIGS. 1A-1H show that mice may be generated with striata chimeric for human HD ESC-derived glia. The striata of neonatally-engrafted rag1 null mice were efficiently colonized with donor hESC hGPCs, which differentiated as astroglia in both striatal gray and white matter.

The disclosure herein relates generally to a non-human mammal model of a human neurodegenerative disorder, methods of producing a non-human mammal model of a human neurodegenerative disorder, methods of identifying an agent suitable for treating a neurodegenerative disorder, methods of treating a neurodegenerative disorder, and methods of restoring normal brain interstitial K$^+$ levels in a subject with dysregulated glial K$^+$ channel function.

Accordingly, a first aspect of the present disclosure relates to a non-human mammal model of a human neurodegenerative disorder, wherein at least 30% of all of the glial cells in its corpus callosum are human glial cells and/or at least 5% of all of the glial cells in the white matter of its brain and/or brain stem are human neurodegenerative disorder specific glial cells.

Another aspect relates to a method of producing a non-human mammal model of a human neurodegenerative disorder. This method involves providing a population of isolated human neurodegenerative disorder specific glial cells; introducing the population of isolated human neurodegenerative disorder specific glial cells into multiple locations within the forebrain and/or brain stem of the non-human mammal; and recovering the non-human mammal with the human neurodegenerative disorder specific glial cells replacing native glial cells in the brain.

The non-human mammal model described herein is a model of a human neurodegenerative disorder. A neurodegenerative disorder or a neurodegenerative disease is a chronic progressive neuropathy characterized by selective and generally symmetrical loss of neurons in motor, sensory, or cognitive systems. Exemplary non-human mammal models of neurodegenerative disease include, without limitation, a Huntington's disease model, degenerative dementia model, Alzheimer's disease model, frontotemporal dementia model, and amyotrophic lateral sclerosis model.

Huntington's disease is an autosomal dominant neurodegenerative disease characterized by a relentlessly progressive movement disorder with devastating psychiatric and cognitive deterioration. Huntington's disease is associated with a consistent and severe atrophy of the neostriatum which is related to a marked loss of the GABAergic medium-sized spiny projection neurons, the major output neurons of the striatum. Huntington's disease is characterized by abnormally long CAG repeat expansions in the first exon of the Huntingtin gene ("HTT"). The encoded polyglutamine expansions of mutant huntingtin protein disrupt its normal functions and protein-protein interactions, ultimately yielding widespread neuropathology, most rapidly evident in the neostriatum.

Alzheimer's disease ("AD") is a progressive, degenerative brain disease that slowly erodes memory and thinking skills, and eventually even the ability to carry out simple tasks. It is the most common cause of dementia.

Frontotemporal dementia is a group of related conditions resulting from the progressive degeneration of the temporal and frontal lobes of the brain. These areas of the brain play a significant role in decision-making, behavioral control, emotion, and language.

Amyotrophic lateral sclerosis (ALS, commonly called "Lou Gehrig's disease") is the most common motor neuron disease in adults. Motor neuron diseases are neurodegenerative diseases that cause selective loss of the nerve cells that directly connect the brain to muscles.

The non-human mammal model described herein can be any neonatal, juvenile, or adult non-human mammal. Exemplary non-human mammals include mice, rats, guinea pigs and other small rodents, dogs, cats, sheep, goats, and monkeys. In one embodiment, the non-human mammal is a mouse. Suitable strains of mice include, without limitation, CD-1® Nude mice, NU/NU mice, BALB/C Nude mice, BALB/C mice, NIH-III mice, SCID® mice, outbred SCID® mice, SCID Beige mice, C3H mice, C57BL/6 mice, DBA/2 mice, FVB mice, CB17 mice, 129 mice, SJL mice, B6C3F1 mice, BDF1 mice, CDF1 mice, CB6F1 mice, CF-1 mice, Swiss Webster mice, SKH1 mice, PGP mice, and B6SJL mice.

In one embodiment, the non-human mammal is hypomyelinated. Hypomyelinated mammals comprise an abnormally reduced amount of myelin. In another embodiment, the non-human mammal has normal levels of myelin throughout its brain and brainstem.

As used herein, the term "glial cells" refers to a population of non-neuronal cells that provide support and nutrition, maintain homeostasis, either form myelin or promote myelination, and participate in signal transmission in the nervous system. "Glial cells" as used herein encompasses fully differentiated cells of the glial lineage, such as oligodendrocytes or astrocytes, and well as glial progenitor cells. Glial progenitor cells are cells having the potential to differentiate into cells of the glial lineage such as oligodendrocytes and astrocytes.

As used herein, the term "white matter" relates to a component of the central nervous system, in the brain and superficial spinal cord, which consists mostly of glial cells and myelinated axons that transmit signals from one region of the cerebrum to another and between the cerebrum and lower brain centers.

In one embodiment, at least 5% of all the glial cells in the white matter of the non-human mammal's brain and/or brain stem are human neurodegenerative disorder specific glial cells. In one embodiment, at least 15% of all the glial cells in the white matter of the non-human mammal's brain and/or brain stem are human neurodegenerative disorder specific glial cells. In another embodiment, at least 30% or more of all the glial cells in the white matter of the non-human mammal's brain and/or brain stem are human neurodegenerative disorder specific glial cells. In another embodiment, at least 50% or more of all the glial cells in the white matter of the non-human mammal's brain and/or brain stem are human neurodegenerative disorder specific glial cells. In one embodiment, at least 70% of all the glial cells in the white matter of the non-human mammal's brain and/or brain stem are human neurodegenerative disorder specific glial cells.

In another embodiment, the white matter of the non-human mammal is cerebellar white matter and at least 50% of all glial cells in the cerebellar white matter are human neurodegenerative disorder specific glial cells. In another embodiment, at least 70% or more of all glial cells in the cerebellar white matter are human neurodegenerative disorder specific glial cells.

In another embodiment, at least 30% of the glial cells in the corpus callosum of the non-human mammal are human neurodegenerative disorder specific glial cells. In another embodiment, at least 50% of all of the glial cells in the corpus callosum of the non-human mammal are human neurodegenerative disorder specific glial cells. In another embodiment, at least 70% of all of the glial cells in the corpus callosum of the non-human mammal are human neurodegenerative disorder specific glial cells. In yet another embodiment, at least 90% of all the glial cells in the corpus callosum of the non-human mammal are human neurodegenerative disorder specific glial cells.

The human neurodegenerative disorder specific glial cells of the non-human mammal described herein exhibit glial cell pathology, e.g., glial cell specific gene expression, growth, structure, organization, differentiation, proliferation, and the like that is associated with the neurodegenerative disorder. Similarly, the non-human mammal model of the human neurodegenerative disease as described herein exhibits at least some of the pathological, physiological, and behavioral characteristics and phenotypes associated with the human neurodegenerative disorder. For example, in one embodiment the non-human mammal model is a model of Huntington's disease. In this embodiment, the mammal model exhibits significantly slower motor learning and decrements in motor coordination, which is characteristic of Huntington's disease, as compared to non-human healthy mammals (i.e., non-human mammals comprising non-diseased human glial cells). Likewise, striatal neurons of the non-human mammal model of Huntington's disease exhibit increased neuronal excitability and decreased input resistance compared to striatal neurons of a non-human healthy mammal. This neuronal phenotype is characteristic of the neuronal phenotype in a human patient having Huntington's disease.

In one embodiment, the human neurodegenerative disorder specific glial cells of the non-human mammal model are derived from a human patient having the disorder. In another embodiment, the human neurodegenerative disorder specific glial cells of the non-human mammal model are engineered to be neurodegenerative disorder specific, i.e., the cells are engineered to contain one or more genetic mutations associated with the neurodegenerative disease and/or increase or decrease expression of one or more disease associated biological molecules (e.g., proteins, polysaccharides, lipids, or nucleic acid molecules). For example, as described herein, an exemplary non-human mammal model of Huntington's disease may comprise human glial cells engineered to express a mutant Huntingtin gene having an expansion of a CAG (cytosine-adenine-guanine) triplet repeat.

The human neurodegenerative disorder specific glial cells of the non-human mammal model described herein may be derived from any suitable source of glial cells, such as, for example and without limitation, human induced pluripotent stem cells (iPSCs), embryonic stem cells, fetal tissue, glial progenitor cells, and/or astrocytes as described in more detail below.

iPSCs are pluripotent cells that are derived from non-pluripotent cells, such as somatic cells. For example, and without limitation, iPSCs can be derived from tissue, peripheral blood, umbilical cord blood, and bone marrow (see e.g., Cai et al., "Generation of Human Induced Pluripotent Stem Cells from Umbilical Cord Matrix and Amniotic Membrane Mesenchymal Cells," *J. Biol. Chem.* 285 (15):112227-11234 (2110); Giorgetti et al., "Generation of Induced Pluripotent Stem Cells from Human Cord Blood Cells with only Two Factors: Oct4 and Sox2," *Nat. Protocol.* 5 (4):811-820 (2010); Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi:10.1093/eurheartj/ehs203 (Jul. 12, 2012); Hu et al., "Efficient Generation of Transgene-Free Induced Pluripotent Stem Cells from Normal and Neoplastic Bone Marrow and Cord Blood Mononuclear Cells," *Blood* doi: 10.1182/blood-2010-07-298331 (Feb. 4, 2011); Sommer et al., "Generation of Human Induced Pluripotent Stem Cells from Peripheral Blood using the STEMCCA Lentiviral Vector," *J. Vis. Exp.* 68:e4327 doi:10.3791/4327 (2012), which are hereby incorporated by reference in their entirety). The somatic cells are reprogrammed to an embryonic stem cell-like state using genetic manipulation. Exemplary somatic cells suitable for the formation of iPSCs include fibroblasts (see e.g., Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi:10.1093/eurheartj/ ehs203 (2012), which is hereby incorporated by reference in its entirety), such as dermal fibroblasts obtained by a skin sample or biopsy, synoviocytes from synovial tissue, keratinocytes, mature B cells, mature T cells, pancreatic β cells, melanocytes, hepatocytes, foreskin cells, cheek cells, or lung fibroblasts.

Methods of producing induced pluripotent stem cells are known in the art and typically involve expressing a combination of reprogramming factors in a somatic cell. Suitable reprogramming factors that promote and induce iPSC generation include one or more of Oct4, Klf4, Sox2, c-Myc, Nanog, C/EBPα, Esrrb, Lin28, and Nr5a2. In certain embodiments, at least two reprogramming factors are expressed in a somatic cell to successfully reprogram the somatic cell. In other embodiments, at least three reprogramming factors are expressed in a somatic cell to successfully reprogram the somatic cell.

iPSCs may be derived by methods known in the art, including the use integrating viral vectors (e.g., lentiviral vectors, inducible lentiviral vectors, and retroviral vectors), excisable vectors (e.g., transposon and foxed lentiviral vectors), and non-integrating vectors (e.g., adenoviral and plasmid vectors) to deliver the genes that promote cell reprogramming (see e.g., Takahashi and Yamanaka, *Cell* 126:663-676 (2006); Okita. et al., *Nature* 448:313-317 (2007); Nakagawa et al., *Nat. Biotechnol.* 26:101-106 (2007); Takahashi et al., *Cell* 131:1-12 (2007); Meissner et al. *Nat. Biotech.* 25:1177-1181 (2007); Yu et al. *Science* 318:1917-1920 (2007); Park et al. *Nature* 451:141-146 (2008); and U.S. Patent Application Publication No. 2008/0233610, which are hereby incorporated by reference in their entirety). Other methods for generating IPS cells include those disclosed in WO2007/069666, WO2009/006930, WO2009/ 006997, WO2009/007852, WO2008/118820, U.S. Patent Application Publication No. 2011/0200568 to Ikeda et al., U.S. Patent Application Publication No 2010/0156778 to Egusa et al., U.S. Patent Application Publication No 2012/ 0276070 to Musick, and U.S. Patent Application Publication No 2012/0276636 to Nakagawa, Shi et al., *Cell Stem Cell* 3 (5):568-574 (2008), Kim et al., *Nature* 454:646-650 (2008), Kim et al., *Cell* 136 (3):411-419 (2009), Huangfu et al., *Nat. Biotechnol.* 26:1269-1275 (2008), Zhao et al., *Cell Stem Cell* 3:475-479 (2008), Feng et al., *Nat. Cell Biol.* 11:197-203 (2009), and Hanna et al., *Cell* 133 (2):250-264 (2008) which are hereby incorporated by reference in their entirety.

The methods of iPSC generation described above can be modified to include small molecules that enhance reprogramming efficiency or even substitute for a reprogramming factor. These small molecules include, without limitation, epigenetic modulators such as, the DNA methyltransferase inhibitor 5'-azacytidine, the histone deacetylase inhibitor VPA, and the G9a histone methyltransferase inhibitor BIX-01294 together with BayK8644, an L-type calcium channel agonist. Other small molecule reprogramming factors include those that target signal transduction pathways, such as TGF-β inhibitors and kinase inhibitors (e.g., kenpaullone) (see review by Sommer and Mostoslavsky, "Experimental Approaches for the Generation of Induced Pluripotent Stem Cells," *Stem Cell Res. Ther.* 1:26 doi:10.1186/scrt26 (Aug. 10, 2010), which is hereby incorporated by reference in its entirety).

Methods of obtaining highly enriched preparations of glial progenitor cells from the iPSCs that are suitable for making the non-human mammal models described herein are disclosed in WO2014/124087 to Goldman and Wang, and Wang et al., "Human iPSC-Derived Oligodendrocyte Progenitors Can Myelinate and Rescue a Mouse Model of Congenital Hypomyelination," *Cell Stem Cell* 12 (2):252-264 (2013), which are hereby incorporated by reference in their entirety.

In another embodiment the human neurodegenerative disorder specific glial cells of the non-human mammal model described herein are derived from embryonic stem cells. Human Embryonic stem cells provide a virtually unlimited source of clonal/genetically modified cells potentially useful for tissue replacement therapies. Methods of obtaining highly enriched preparations of glial progenitor cells from embryonic cells that are suitable for making the non-human mammal model of the present disclosure are described herein as disclosed in Wang et al., "Human iPSC-derived oligodendrocyte progenitor cells can myelinate and rescue a mouse model of congenital hypomyelination," *Cell Stem Cell* 12:252-264 (2013), which is hereby incorporated by reference in its entirety.

In another embodiment, the human glial cells of the non-human mammal are derived from human fetal tissue. Glial progenitor cells can be extracted from fetal brain tissue containing a mixed population of cells directly by using the promoter specific separation technique as described in U.S. Patent Application Publication Nos. 20040029269 and 20030223972 to Goldman, which are hereby incorporated by reference in their entirety. This method involves selecting a promoter which functions specifically in glial progenitor cells, and introducing a nucleic acid encoding a marker protein under the control of said promoter into the mixed population cells. The mixed population of cells is allowed to express the marker protein and the cells expressing the marker protein are separated from the population of cells, with the separated cells being the glial progenitor cells. Human glial progenitor cells can be isolated from ventricular or subventricular zones of the brain or from the subcortical white matter.

Glial specific promoters that can be used for isolating glial progenitor cells from a mixed population of cells include the CNP promoter (Scherer et al., *Neuron* 12:1363-75 (1994), which is hereby incorporated by reference in its entirety), an NCAM promoter (Holst et al., *J. Biol. Chem.* 269:22245-52 (1994), which is hereby incorporated by reference in its entirety), a myelin basic protein promoter (Wrabetz et al., *J. Neurosci. Res.* 36:455-71 (1993), which is hereby incorporated by reference in its entirety), a JC virus minimal core promoter (Krebs et al., *J. Virol.* 69:2434-42 (1995), which is hereby incorporated by reference in its entirety), a myelin-associated glycoprotein promoter (Laszkiewicz et al., "Structural Characterization of Myelin-associated Glycoprotein Gene Core Promoter," *J. Neurosci. Res.* 50 (6): 928-36 (1997), which is hereby incorporated by reference in its entirety), or a proteolipid protein promoter (Cook et al., "Regulation of Rodent Myelin Proteolipid Protein Gene Expression," *Neurosci. Lett.* 137 (1): 56-60 (1992); Wight et al., "Regulation of Murine Myelin Proteolipid Protein Gene Expression," *J. Neurosci. Res.* 50 (6): 917-27 (1997); and Cambi et al., *Neurochem. Res.* 19:1055-60 (1994), which are hereby incorporated by reference in their entirety). See also U.S. Pat. No. 6,245,564 to Goldman et. al., which is hereby incorporated by reference in its entirety.

The glial progenitor cell population derived from fetal tissue can be enriched for by first removing neurons or neural progenitor cells from the mixed cell population. Where neuronal progenitor cells are to be separated from the mixed population of cells, they can be removed based on their surface expression of NCAM, PSA-NCAM, or any other surface moiety specific to neurons or neural progenitor cells. Neurons or neural progenitor cells may also be separated from a mixed population of cells using the promoter based separation technique. Neuron or neural progenitor specific promoters that can be used for separating neural cells from a mixed population of cells include the Tal tubulin promoter (Gloster et al., *J. Neurosci.* 14:7319-30 (1994), which is hereby incorporated by reference in its entirety), a Hu promoter (Park et al., "Analysis of Upstream Elements in the HuC Promoter Leads to the Establishment of Transgenic Zebrafish with Fluorescent Neurons," *Dev. Biol.* 227 (2): 279-93 (2000), which is hereby incorporated by reference in its entirety), an ELAV promoter (Yao et al., "Neural Specificity of ELAV Expression: Defining a Drosophila Promoter for Directing Expression to the Nervous System," *J. Neurochem.* 63 (1): 41-51 (1994), which is hereby incorporated by reference in its entirety), a MAP-1B promoter (Liu et al., *Gene* 171:307-08 (1996), which is hereby incorporated by reference in its entirety), or a GAP-43 promoter. Techniques for introducing the nucleic acid molecules of the construct into the plurality of cells and then sorting the cells are described in U.S. Pat. No. 6,245,564 to Goldman et al., and U.S. Patent Application Publication No. 20040029269 to Goldman et al., which are hereby incorporated by reference in their entirety.

As an alternative to using promoter-based cell sorting to recover glial progenitor cells from a mixed population of cells, an immunoseparation procedure can be utilized. In a positive immunoseparation technique, the desired cells (i.e. glial progenitor cells) are isolated based on proteinaceous surface markers naturally present on the progenitor cells. For example, the surface marker A2B5 is an initially expressed early marker of glial progenitor cells (Nunes et al., "Identification and Isolation of Multipotential Neural Progenitor Cells from the Adult Human White Matter," *Soc. Neurosci. Abstr.* (2001), which is hereby incorporated by reference in its entirety). Using an antibody specific to A2B5, glial progenitor cells can be separated from a mixed population of cell types. Similarly, the surface marker CD44 identifies astrocyte-biased glial progenitor cells (Liu et al., "CD44 Expression Identifies Astrocyte-Restricted Precursor Cells," *Dev. Biol.* 276:31-46 (2004), which is hereby incorporated by reference in its entirety). Using CD44-conjugated microbead technology, astroctye-biased glial progenitor cells can be separated from a mixed population of cell types. Oligodendrocyte-biased glial progenitor cells can be separated from a mixed population of cell types based on expression of PDGFαR, the PDGFαR ectodomain CD140a, or CD9. Cells expressing markers of non-glial cell types (e.g., neurons, inflammatory cells, etc.) can be removed from the preparation of glial cells to further enrich the preparation for the desired glial cell type using immunoseparation techniques. For example, the glial progenitor cell population is preferably negative for a PSA-NCAM marker and/or other markers for cells of neuronal lineage, negative for one or more inflammatory cell markers, e.g., negative for a CD11 marker, negative for a CD32 marker, and/or negative for a CD36 marker, which are markers for microglia. Exemplary microbead technologies include MACS® Microbeads, MACS® Columns, and MACS® Separators. Additional examples of immunoseparation are described in Wang et al., "Prospective Identification, Direct Isolation, and Expression Profiling of a Telomerase Expressing Subpopulation of Human Neural Stem Cells, Using Sox2 Enhancer-Directed FACS," *J. Neurosci.* 30:14635-14648 (2010); Keyoung et al., "High-Yield Selection and Extraction of Two Promoter-Defined Phenotypes of Neural Stem Cells from the Fetal Human Brain," *Nat. Biotechnol.* 19:843-850 (2001); and Windrem et al., "Neonatal Chimerization with Human Glial Progenitor Cells can both Remyelinate and Rescue the Otherwise Lethally Hypomyelinated Shiverer Mouse," *Cell Stem Cell* 2:553-565 (2008), which are hereby incorporated by reference in their entirety.

In accordance with the method of producing the non-human mammal model of a human neurodegenerative disorder, the selected preparation of administered human neurodegenerative disorder specific glial cells comprise at least about 80% glial cells, including, for example, about 80%, 85%, 90%, 95%, 96%, 97%, 98%, 99%, 100% glial cells. The selected preparation of glial cells can be relatively devoid (e.g., containing less than 20, 15, 10, 9, 8, 7, 6, 5, 4, 3, 2, or 1%) of other cells types such as neurons or cells of neuronal lineage, fibrous astrocytes and cells of fibrous astrocyte lineage, and pluripotential stem cells (like ES cells). Optionally, example cell populations are substantially pure populations of glial cells.

To produce the non-human mammal model described herein, a population of isolated human neurodegenerative disorder specific glial cells is introduced into multiple locations within the forebrain and/or brain stem of a non-human mammal. The population of cells introduced may be a population of glial progenitor cells and/or astrocyte cells. As described above, the glial progenitor cells and/or astrocytes can be derived from any suitable source, e.g., iPSCs, embryonic stem cells, fetal tissue, glial progenitor cells. As described supra, the glial progenitor cells and/or astrocytes can be derived from a patient having the neurodegenerative disease. Alternatively, the glial progenitor cells or astrocytes are engineered to a neurodegenerative disorder specific state. Suitable methods of introducing cells into the forebrain and/or brain stem of non-human mammals are well known to those of skill in the art and include, but are not limited to, injection, deposition, and grafting as described herein.

In one embodiment, the glial progenitor cells are transplanted bilaterally into multiple sites of the non-mammal host animal as described U.S. Pat. No. 7,524,491 to Goldman, Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), Han et al., "Forebrain Engraftment by Human Glial Progenitor Cells Enhances Synaptic Plasticity and Learning Adult Mice," *Cell Stem Cell* 12:342-353 (2013), and Wang et al., "Human iPSCs-Derived Oligodendrocyte Progenitor Cells Can Myelinate and Rescue a Mouse Model of Congenital Hypomyelination," *Cell Stem Cell* 12:252-264 (2013), which are hereby incorporated by reference in their entirety). Methods for transplanting nerve tissues and cells into host brains are described by Bjorklund and Stenevi (eds), Neural Grafting in the Mammalian CNS, Ch. 3-8, Elsevier, Amsterdam (1985); U.S. Pat. No. 5,082,670 to Gage et al.; and U.S. Pat. No. 6,497,872 to Weiss et al., which are hereby incorporated by reference in their entirety. Typical procedures include intraparenchymal, intracallosal, intraventricular, intrathecal, and intravenous transplantation.

Intraparenchymal transplantation is achieved by injection or deposition of tissue within the host brain so as to be apposed to the brain parenchyma at the time of transplantation. The two main procedures for intraparenchymal transplantation are: 1) injecting the donor cells within the host brain parenchyma or 2) preparing a cavity by surgical means to expose the host brain parenchyma and then depositing the graft into the cavity (Bjorklund and Stenevi (eds), *Neural Grafting in the Mammalian CNS*, Ch. 3, Elsevier, Amsterdam (1985), which is hereby incorporated by reference in its entirety). Both methods provide parenchymal apposition between the donor cells and host brain tissue at the time of grafting, and both facilitate anatomical integration between the graft and host brain tissue. This is of importance if it is required that the donor cells become an integral part of the host brain and survive for the life of the host.

Glial progenitor cells can also be delivered intracallosally as described in U.S. Patent Application Publication No. 20030223972 to Goldman, which is hereby incorporated by reference in its entirety. The glial progenitor cells can also be delivered directly to the forebrain subcortex, specifically into the anterior and posterior anlagen of the corpus callosum. Glial progenitor cells can also be delivered to the cerebellar peduncle white matter to gain access to the major cerebellar and brainstem tracts. Glial progenitor cells can also be delivered to the spinal cord.

Alternatively, the cells may be placed in a ventricle, e.g., a cerebral ventricle. Grafting cells in the ventricle may be accomplished by injection of the donor cells or by growing the cells in a substrate such as 30% collagen to form a plug of solid tissue which may then be implanted into the ventricle to prevent dislocation of the graft cells. For subdural grafting, the cells may be injected around the surface of the brain after making a slit in the dura.

As indicated supra, the isolated population of human neurodegenerative disorder specific glial cells are introduced into a myelin deficient or myelin depleted non-human mammal. Alternatively, the isolated population of human neurodegenerative disorder specific glial cells are introduced into a normally myelinated non-human mammal.

It is desirable that the non-human mammal host accepts the human glial cells with little or no adverse immune recognition. Therefore, in some embodiments, the non-human mammal is immuno-incompetent, immuno-deficient, or immuno-suppressed.

Immunosuppression can be achieved either through the administration of immunosuppressive drugs such as cyclosporin, sirolimus, or tacrolimus, or through strategies employing locally applied immunosuppressants. Local immunosuppression is disclosed by Gruber, *Transplantation* 54:1-11 (1992), which is hereby incorporated by reference in its entirety. U.S. Pat. No. 5,026,365 to Rossini, which is hereby incorporated by reference in its entirety, discloses encapsulation methods also suitable for local immunosuppression.

As an alternative to employing immunosuppression techniques, methods of gene replacement or knockout using homologous recombination, as taught by Smithies et al. *Nature* 317:230-234 (1985), which is hereby incorporated by reference in its entirety, can be applied to donor glial cells for the ablation of major histocompatibility complex (MHC) genes. Donor glial cells lacking MHC expression allows the transplantation of an enriched glial cell population across allogeneic and perhaps even xenogenic histocompatibility barriers without the need to immunosuppress the recipient. Other suitable recombinant methods to reduce antigenicity of the human glial cells in the non-human mammal as described herein are also disclosed by Gruber, *Transplantation* 54:1-11 (1992), which is hereby incorporated by reference in its entirety. Exemplary approaches to reduce immunogenicity of the human glial cells by surface modification are disclosed in WO92/04033 to Faustman, which is hereby incorporated by reference in its entirety.

Alternatively, the immunogenicity of the transplanted cells may be reduced by using any non-human mammal host that possesses a genetic mutation rendering it immunodeficient. Exemplary animal models include those having a mutation which disrupts the recombination activating gene 2 (Rag2) (Shinkai et al., *Cell* 68:855-867 (1992), which is hereby incorporated by reference in its entirety) or the Rag1 gene (Mombaerts et al., *Cell* 68:869-877 (1992) and Schultz et al., *Transplantation* 76:1036-42 (2003), which are hereby incorporated by reference in their entirety). Other immuno-deficient animal models include any of the severe combined immunodeficient mice ("SCID"), having a mutation in the Prkdc gene. Exemplary SCID mouse models include the NOD-SCID, the NOD-SCID-IL2rg, and the NOG ("NOD-SCID/$\gamma c^{null}$") mouse models. Additionally, the nude mouse models, carrying a mutation in the Foxn1 gene are also useful non-human mammals.

After the population of isolated human neurodegenerative disorder specific glial cells is introduced into the forebrain and/or brain stem of the non-human mammal, the non-human mammal is recovered. As used herein, the term "recovering the non-human mammal" refers to a process or means by which the introduced human glial cells are allowed to functionally engraft into the brain of the non-human mammal. Exemplary percentages of human glial cells present in the white matter and/or corpus callosum of the brain and brain stem of the recovered non-human mammal model are described supra.

Another aspect of the present disclosure relates to a method of identifying an agent suitable for treating a neurodegenerative disorder. This method involves providing a non-human mammal model of a neurodegenerative disorder as described supra and providing a candidate agent. The method further includes administering the candidate agent to the non-human mammal and assessing, as a result of said administering, the therapeutic potential of the candidate agent as suitable for treating the neurodegenerative disorder.

The non-human mammal model of a human neurodegenerative disorder is described supra. Exemplary neurodegenerative disorder models include, without limitation, a model of Huntington's disease, a model of Alzheimer's disease, a model of frontotemporal dementia, and a model of amyotrophic lateral sclerosis. Accordingly, candidate agents suitable for treating any one of these neurodegenerative diseases are identified using the methods described herein.

A candidate agent can be a peptide, nucleic acid molecule, or small molecule compound. More generally, the term "candidate agent" means a substance that has the potential of affecting the function of an organism. Such an agent may be, for example, a naturally occurring, semi-synthetic, or synthetic agent. For example, the candidate agent may be a drug that targets a specific function of an organism. A candidate agent also may be a nutrient. A candidate agent may decrease, suppress, attenuate, diminish, arrest, or stabilize the development or progression of a neurodegenerative disease, disorder, or condition in a host organism.

Candidate agents may be obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily modified through conventional chemical, physical, and biochemical means. Further, known agents may be subjected to directed or random chemical modifications such as acylation, alkylation, esterification, amidification, etc. to produce structural analogs of the agents.

Candidate agents can be administered via any standard route of administration known in the art, including, but not limited to, parenteral (e.g., intravenous, intraarterial, intramuscular, subcutaneous injection, intrathecal), oral (e.g., dietary), topical, transmucosal, or by inhalation (e.g., intrabronchial, intranasal or oral inhalation, intranasal drops).

The step of assessing may involve determining the behavior or fate of the human neurodegenerative disorder specific glial cells or other neuronal cells affected by the neurodegenerative disease using a suitable metric that is indicative of the therapeutic efficacy of the candidate agent. For example, assessing may involve examination of cell morphology, immunophenotype, transcriptionally-regulated reporters, gene expression profiles, mitotic rate, mitotic fraction, metabolic rate, mitochondrial function, oxidative state, telomerase activity, apoptotic index, or net cell survival.

When assessing involves examining cellular morphology, the assessment can include measurements of the cell size, fiber outgrowth, length, complexity. Such measurements can be carried out using standard neurohistological techniques known in the art. Typically, such analyses include examining various sections of brain tissue that have been processed according to the histological method employed and labeled with one or more cell specific or nucleic acid markers to aid in examination and measurements. Measurements can be performed using bright field or fluorescent microscopy, confocal microscopy, or electron microscopy depending on the particular endpoint to be measured.

Another aspect of the present disclosure relates to a method of treating a neurodegenerative disorder selected from the group consisting of Huntington's disease, Alzheimer's disease, frontotemporal dementia, and amyotrophic lateral sclerosis in a subject. This method involves selecting a subject having the neurodegenerative disorder and administering to the selected subject a preparation of glial progenitor cells at a dosage effective to treat the neurodegenerative disorder in the subject.

The subject can, for example, have or be at risk of developing (i) a neurological disease, disorder, or condition, e.g., Huntington's disease, Alzheimer's disease, frontotemporal dementia, and/or ALS; (ii) a condition of the nervous system that is secondary to the neurological disease, disorder, or condition; and/or (iii) an injury to the nervous system, such as, for example, an injury caused by physical, mechanical, or chemical trauma that is associated with the aforementioned neurological disease.

As used herein, "treating" or "treatment" refers to any indication of success in amelioration of an injury, pathology, or condition, including any objective or subjective parameter such as abatement; remission; diminishing of symptoms or making the injury, pathology, or condition more tolerable to the patient; slowing the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" includes the administration of glial progenitor cells to prevent or delay, to alleviate, or to arrest or inhibit development of the symptoms or conditions associated with the disease, condition or disorder. "Therapeutic effect" refers to the reduction, elimination, or prevention of the disease, symptoms of the disease, or side effects of a disease, condition or disorder in the subject. Treatment may be prophylactic (to prevent or delay the onset or worsening of the disease, condition or disorder, or to prevent the manifestation of clinical or subclinical symptoms thereof) or therapeutic suppression or alleviation of symptoms after the manifestation of the disease, condition or disorder.

Autologous, allogenic, or xenogenic cells can be used in the administrating step. The glial cells and/or glial progenitor cells can be derived from various sources as described above. Autologous glial cells or iPSCs can be harvested, for example, from the subject. Allogenic glial progenitor cells or iPSCs, for example, can be harvested from donors or donor sources having suitable immunohistocompatibility. Xenogeneic cells can be harvested from a pig, monkey, or any other suitable mammal. The administered cells are optionally immortalized. Cell lines of stem cells and differentiated cells can be used to derive the glial progenitor cells to avoid the use of embryonic tissue and/or glial tissue.

The glial progenitor cells of the administered preparation can optionally be genetically modified to express other proteins of interest. For example, the glial progenitor cells may be modified to express a therapeutic biological molecule, an exogenous targeting moiety, an exogenous marker (for example, for imaging purposes), or the like. The glial progenitor cells of the preparations can be optionally modified to overexpress an endogenous biological molecule, targeting moiety, and/or marker.

The glial progenitor cells of the administered preparation may be astrocyte biased glial progenitor cells, oligodendrocyte-biased glial progenitor cells, unbiased glial progenitor cells, or a combination thereof. The glial progenitor cells of the administered preparation express one or more markers of the glial cell lineage. For example, in one embodiment, the glial progenitor cells of the administered preparation may express A2B5$^+$. In another embodiment, glial progenitor cells of the administered preparation are positive for a PDGFαR marker. The PDGFαR marker is optionally a PDGFαR ectodomain, such as CD140a. PDGFαR and CD140a are markers of an oligodendrocyte-biased glial progenitor cells. In another embodiment, glial progenitor cells of the administered preparation are CD44$^+$. CD44 is a marker of an astrocyte-biased glial progenitor cell. In another embodiment, glial progenitor cells of the administered preparation are positive for a CD9 marker. The CD9 marker is optionally a CD9 ectodomain. In one embodiment, the glial progenitor cells of the preparation are A2B5$^+$, CD140a$^+$, and/or CD44$^+$. The aforementioned glial progenitor cell surface markers can be used to identify, separate, and/or enrich the preparation for glial progenitor cells prior to administration.

The administered glial progenitor cell preparation is optionally negative for a PSA-NCAM marker and/or other neuronal lineage markers, and/or negative for one or more inflammatory cell markers, e.g., negative for a CD11 marker, negative for a CD32 marker, and/or negative for a CD36 marker (which are markers for microglia). Optionally, the preparation of glial progenitor cells are negative for any combination or subset of these additional markers. Thus, for example, the preparation of glial progenitor cells is negative for any one, two, three, or four of these additional markers.

Suitable techniques for glial cell delivery are described supra. In one embodiment, said preparation of glial progenitor cells is administered to the striatum, forebrain, brain stem, and/or cerebellum of the subject.

Delivery of the cells to the subject can include either a single step or a multiple step injection directly into the nervous system. For localized disorders such as demyelination of the optic nerve, a single injection can be used. Although adult and fetal oligodendrocyte precursor cells disperse widely within a transplant recipient's brain, for widespread disorders, multiple injections sites can be performed to optimize treatment. Injection is optionally directed into areas of the central nervous system such as white matter tracts like the corpus callosum (e.g., into the anterior and posterior anlagen), dorsal columns, cerebellar peduncles, cerebral peduncles. Such injections can be made unilaterally or bilaterally using precise localization methods such as stereotaxic surgery, optionally with accompanying imaging methods (e.g., high resolution MRI imaging). One of skill in the art recognizes that brain regions vary across species; however, one of skill in the art also recognizes comparable brain regions across mammalian species.

The cellular transplants are optionally injected as dissociated cells but can also be provided by local placement of non-dissociated cells. In either case, the cellular transplants optionally comprise an acceptable solution. Such acceptable solutions include solutions that avoid undesirable biological activities and contamination. Suitable solutions include an appropriate amount of a pharmaceutically-acceptable salt to render the formulation isotonic. Examples of the pharmaceutically-acceptable solutions include, but are not limited to, saline, Ringer's solution, dextrose solution, and culture media. The pH of the solution is preferably from about 5 to about 8, and more preferably from about 7 to about 7.5.

The injection of the dissociated cellular transplant can be a streaming injection made across the entry path, the exit path, or both the entry and exit paths of the injection device (e.g., a cannula, a needle, or a tube). Automation can be used to provide a uniform entry and exit speed and an injection speed and volume.

The number of glial progenitor cells administered to the subject can range from about $10^2$-$10^8$ at each administration (e.g., injection site), depending on the size and species of the recipient, and the volume of tissue requiring cell replacement. Single administration (e.g., injection) doses can span ranges of $10^3$-$10^5$, $10^4$-$10^7$, and $10^5$-$10^8$ cells, or any amount in total for a transplant recipient patient.

Since the CNS is an immunologically privileged site, administered cells, including xenogeneic, can survive and, optionally, no immunosuppressant drugs or a typical regimen of immunosuppressant agents are used in the treatment methods. However, optionally, an immunosuppressant agent may also be administered to the subject. Immunosuppressant agents and their dosing regimens are known to one of skill in the art and include such agents as Azathioprine, Azathioprine Sodium, Cyclosporine, Daltroban, Gusperimus Trihydrochloride, Sirolimus, and Tacrolimus. Dosages ranges and duration of the regimen can be varied with the disorder being treated; the extent of rejection; the activity of the specific immunosuppressant employed; the age, body weight, general health, sex and diet of the subject; the time of administration; the route of administration; the rate of excretion of the specific immunosuppressant employed; the duration and frequency of the treatment; and drugs used in combination. One of skill in the art can determine acceptable dosages for and duration of immunosuppression. The dosage regimen can be adjusted by the individual physician in the event of any contraindications or change in the subject's status.

When the neurodegenerative disease to be treated is Huntington's disease, the method may further involve administering one or more reagents capable of inducing medium spiny neuron addition in conjunction with said administering of the preparation of glial progenitor cells. In accordance with this embodiment, said one or more reagents is selected from the group consisting of brain-derived neurotrophic factor, noggin, neurotrophin-4 ("NT-4"), insulin-like growth factor-1, or a combination thereof. Likewise, when treating other neurodegenerative diseases, the glial progenitor cells can be administered in combination with one or more other commonly administered disease specific therapeutics.

Suitable subjects for treatment in accordance with the methods described herein include any mammalian subject having a neurodegenerative disorder. Exemplary mammalian subjects include humans, mice, rats, guinea pigs, and other small rodents, dogs, cats, sheep, goats, and monkeys. In one embodiment, the subject is human.

Another aspect relates to a method of restoring normal brain interstitial K$^+$ levels in a subject with dysregulated glial K$^+$ channel function. This method involves selecting a subject having dysregulated glial K$^+$ plus channel function and administering to the selected subject a preparation of glial progenitor cells at a dosage effective to restore normal brain interstitial glial K$^+$ levels in the selected subject.

Ion channels are transmembrane proteins that regulate the flow of ions across biological membranes. Potassium channels ("K+ channels") represent the most diverse group of ion channels and are comprised of four structural types based on their mode of activation and the number of their transmembrane segments ("TM"): inwardly rectifying 2 TM K+ channels ("Kir"), two-pore 4 TM K+ channels ("K2P"), calcium-activated 6 or 7 TM K+ channels ("KCa"), and voltage-gated 6 TM K+ channels ("KV").

Three major subfamilies or Kir K+ channels have been identified: Kir1, Kir2, and Kir3 (ROMK, IRK and GIRK, respectively) (Gutman et al., International Union of Pharmacology. XLI. Compendium of Voltage-Gated Ion Channels: Potassium Channels. *Pharmacol. Rev.* 55:583-586 (2003); Karschin et al., "IRK (1-3) and GIRK (1-4) Inwardly Rectifying K+ Channel mRNAs are Differentially Expressed in the Adult Rat Brain," *J. Neurosci.* 16:3559-3570 (1996); and Lesage et al., "Cloning Provides Evidence for a Family of Inward Rectifier and G-Protein-Coupled K+ Channels in the Brain," *FEBS Lett* 353:37-42 (1994), which are hereby incorporated by reference in their entirety). Kir channels assemble as heteromeric complexes in the membrane. Kir1 channels are only "mildly" rectifying, whereas Kir2 channels underlie "strong" inward rectification and are the principal contributors of measured inward K+ currents detected in the striatum (Karschin et al., "IRK (1-3) and GIRK (1-4) Inwardly Rectifying K+ Channel mRNAs are Differentially Expressed in the Adult Rat Brain," *J. Neurosci.* 16:3559-3570 (1996) and Mermelstein et al., "Inwardly Rectifying Potassium (IRK) Currents are Correlated with IRK Subunit Expression in Rat Nucleus Accumbens Medium Spiny Neurons," *J. Neurosci.* 18:6650-6661 (1998), which are hereby incorporated by reference in their entirety). Kir3 channels are subject to G protein activation and are expressed in lower abundance in the striatum (Karschin et al., "IRK (1-3) and GIRK (1-4) Inwardly Rectifying K+ Channel mRNAs are Differentially Expressed in the Adult Rat Brain," *J. Neurosci.* 16:3559-3570 (1996), which is hereby incorporated by reference in its entirety).

Voltage-gated potassium channels mediate depolarization-activated K+ currents (Bertil Hille, *Ionic Channels of Excitable Membranes* (3d ed., Sinauer 2001), which is hereby incorporated by reference in its entirety). Three types of outward K+ currents have been described in MSNs (Nisenbaum et al., "Isolation and Characterization of a Persistent Potassium Current in Neostriatal Neurons," *J. Neurophysiol.* 76:1180-1194 (1996) and Surmeier et al., "Developmental Regulation of a Slowly Inactivating Potassium Conductance in Rat Neostriatal Neurons," *Neurosci. Lett.* 122:41-46 (1991), which are hereby incorporated by reference in their entirety). Two of these outward currents are fast or slowly inactivating conductances and are sensitive to 4-aminopyridine. The third outward current, the delayed rectifier, is non-inactivating or persistent, is detected at relatively depolarized potentials, and can be blocked by the addition of tetraethylammonium (Ashcroft et al., "Voltage-gated K+ Channels," in *Ion Channels and Disease.* San Diego, Calif.: Academic: 97-125 (2000), which is hereby incorporated by reference in its entirety).

Importantly, potassium channels help maintain medium spiny neurons (MSN) in the hyperpolarized state (Bargas et al., "Electrotonic Properties of Neostriatal Neurons are Modulated by Extracellular Potassium," *Exp. Brain Res.* 72:390-398 (1988), which is hereby incorporated by reference in its entirety), contribute to the regulation of firing (Bargas et al., "An Early Outward Conductance Modulates the Firing Latency and Frequency of Neostriatal Neurons of the Rat Brain," *Exp. Brain Res.* 75:146-156 (1989); Nisenbaum et al., "Potassium Currents Responsible for Inward and Outward Rectification in Rat Neostriatal Spiny Projection Neurons," *J. Neurosci.* 15:4449-446; and Nisenbaum et al., "Isolation and Characterization of a Persistent Potassium Current in Neostriatal Neurons," *J. Neurophysiol.* 76:1180-1194 (1996), which are hereby incorporated by reference in their entirety), and confer unique physiological profiles to striatal MSNs and interneurons (Mermelstein et al., "Inwardly Rectifying Potassium (IRK) Currents are Correlated with IRK Subunit Expression in Rat Nucleus Accumbens Medium Spiny Neurons," *J. Neurosci.* 18:6650-6661 (1998); Song et al., "Somatodendritic Depolarization-Activated Potassium Currents in Rat Neostriatal Cholinergic Interneurons are Predominantly of the A Type and Attributable to Coexpression of Kv4.2 and Kv4.1 Subunits," *J. Neurosci.* 18 (9):3124-37 (1998); Tkatch et al., "Kv4.2 mRNA Abundance and A-Type K($^+$) Current Amplitude are Linearly Related in Basal Ganglia and Basal Forebrain Neurons," *J. Neurosci.* 20 (2):579-88 (2000); and Wilson et al., "The Origins of Two-State Spontaneous Membrane Potential Fluctuations of Neostriatal Spiny Neurons," *J. Neurosci.* 16 (7):2397-410 (1996), which are hereby incorporated in their entirety). In one embodiment, the dysregulated glial K+ channel function is characterized by defective K+ conductance, defective K+ uptake, and/or defective K+ channel expression.

Suitable preparations of glial progenitor cells and methods of administering these preparations are described above. In one embodiment, the glial progenitor cells are astrocyte-biased glial progenitor cells and express CD44+, A2B5+, CD140a+, or a combination thereof.

EXAMPLES

The examples below are intended to exemplify the practice of embodiments of the disclosure but are by no means intended to limit the scope thereof.

Materials and Methods for Examples 1-7

Isolation of Fetal Human Astroglial Progenitor Cells:

Human fetal brain tissue was obtained from aborted fetuses (18-22 weeks g.a.) under protocols approved by the University of Rochester-Strong Memorial Hospital Research Subjects Review Board. Briefly, forebrain tissue was minced and dissociated using papain and DNase as previously described (see Wang et al., "Prospective Identification, Direct Isolation, and Expression Profiling of a Telomerase Expressing Subpopulation of Human Neural Stem Cells, Using Sox2 Enhancer-Directed FACS," *J. Neurosci.* 30:14635-14648 (2010); Keyoung et al., "High-Yield Selection and Extraction of Two Promoter-Defined Phenotypes of Neural Stem Cells from the Fetal Human Brain," *Nat. Biotechnol.* 19:843-850 (2001); and Windrem et al., "Neonatal Chimerization with Human Glial Progenitor Cells can both Remyelinate and Rescue the Otherwise Lethally Hypomyelinated Shiverer Mouse," *Cell Stem Cell* 2:553-565 (2008), which are hereby incorporated by reference in their entirety) always within 2 hrs of extraction. The dissociated cells were maintained overnight in DMEM/F12/N1-based medium supplemented with 10 ng/ml FGF2. Astrocyte-biased glial progenitor cells were isolated from the tissue dissociates using MACS® targeting the astroglial hyaluronate receptor CD44 (Liu et al., "CD44 Expression Identifies Astrocyte-Restricted Precursor Cells," *Dev Biol.* 276:31-46 (2004), which is hereby incorporated by reference in its entirety) using conjugated microbeads (Miltenyi) according to the manufacturer's instructions. Immediately after sorting, the cells were resuspended in DMEM/F12/N1 supplemented with 10 ng/ml bFGF and 2% PD-FBS at a concentration of $2.5 \times 10^5$ cells/ml in 6 well suspension plates.

Production of mHtt-Transduced Glial Progenitor Cells:

To express mutant vs. control Htt in human GPCs, a self-inactivating lentiviral system (Zufferey et al., "Self-Inactivating Lentivirus Vector for Safe and Efficient in vivo Gene Delivery," *J. Virol.* 72:9873-9880 (1998), which is hereby incorporated by reference in its entirety) was used to over-express either mutant (73Q) or normal (23Q) Htt. To this end, a plasmid (pTANK-CMVie-Htt-IRES-LckEGFP-WPRE) was constructed to carry, in the 5' to 3' direction, the cPPT element (Zennou et al., "The HIV-1 DNA Flap Stimulates HIV Vector-Mediated Cell Transduction in the Brain," *Nat Biotechnol* 19: 446-450 (2001), which is hereby incorporated by reference in its entirety); the cytomegalovirus immediate early promoter; the expression cassette of the first exon of the huntingtin gene and membrane-bounded EGFP, expressed in tandem under the Internal Ribosome Entry Site (IRES) (Jang et al., "A Segment of the 5' Nontranslated Region of Encephalomyocarditis Virus RNA Directs Internal Entry of Ribosomes During In vitro Translation," *J. Virol.* 62:2636-2643 (1988), which is hereby incorporated by reference in its entirety), and the Woodchuck Hepatitis Virus Posttranscriptional Regulatory Element (WPRE) (Zufferey et al., "Woodchuck Hepatitis Virus Posttranscriptional Regulatory Element Enhances Expression of Transgenes Delivered by Retroviral Vectors," *J. Virol.* 73:2886-2892 (1999), which is hereby incorporated by reference in its entirety). The control virus expressed only LckEGFP. Virus particles pseudotyped with vesicular stomatitis virus G glycoprotein were produced, concentrated by ultracentrifugation, and titrated on 293HEK cells. Following fetal cell dissociation and CD44-based immunomagnetic sorting, the cells were transduced with Lenti-htt23Q-LckEGFP, Lenti-htt73Q-LckEGFP or Lenti-LckEGFP control virus, each at 5 MOI (multiplicities of infection). Transduced cells were isolated 5 days later, following EGFP-directed FACS. Cells were then maintained in suspension in low serum and bFGF-containing media prior to transplant.

Production of GPCs from Embryonic Stem Cells:

Glial progenitor cells were generated from human ES cells using previously described protocols (Wang et al., "Human iPSC-Derived Oligodendrocyte Progenitor Cells can Myelinate and Rescue a Mouse Model of Congenital Hypomyelination," *Cell Stem Cell* 12:252-264 (2013), which is hereby incorporated by reference in its entirety). Cells were harvested between 160-240 days in vitro, by which time the majority typically expressed the bipotential glial progenitor cell marker CD140a, while the remainder were A2B5$^+$/CD140a$^-$ astroctyes. Human ES cells were obtained from GENEA, Inc. (Sydney, Australia), as lines GENEA19 (normal Htt: 18 CAG) and GENEA 20 (mutant Htt: 48 CAG), which were derived as a sibling pair from one couple (Bradley et al., "Derivation of Huntington's Disease-Affected Human Embryonic Stem Cell Lines," *Stem Cells Dev.* 20 (3): 495-502 (2011), which is hereby incorporated by reference in its entirety).

Animals:

R6/2×rag1$^{-/-}$ mice are heterozygous transgenic R6/2 mice (Mangiarini et al., "Exon 1 of the HD Gene with an Expanded CAG Repeat is Sufficient to Cause a Progressive Neurological Phenotype in Transgenic Mice," *Cell* 87:493-506 (1996), which is hereby incorporated by reference in its entirety), transgenic for the 5' end of the human Huntingtin gene and bearing a 120±5 CAG repeat expansion in the first exon of the HTT gene, then bred with rag1$^{-/-}$ homozygous immunodeficient mice. The mice were bred through consecutive transplantation of R6/2 ovaries derived from R6/2× rag1$^{-/-}$ mice into wild type females at Jackson Laboratories (Bar Harbor, Me.). The mice were on a hybrid background (C57BL/6×CBAF1/J). Genotyping was performed by PCR analysis of genomic DNA isolated from tail clippings following the Jackson Laboratories genotyping protocol. The mice were socially housed under microisolator conditions, with ad lib access to food and water. All procedures were performed in agreement with protocols approved by the University of Rochester Committee on Animal Resources.

Cell Preparation for Transplantation:

CD44-expressing glial progenitor cells, biased to astrocyte fate (Liu et al., "CD44 Expression Identifies Astrocyte-Restricted Precursor Cells," *Dev. Biol.* 276:31-46 (2004), which is hereby incorporated by reference in its entirety), were passaged with TrypLE 3-5 days prior to transplantation into R6/2 mice. The passaged cells were plated at a density of 100,000-150,000 cells/ml into 100 mm ultra low attachment plates in the media described above to allow small cell clusters (100-200 μm in diameter). To prepare cells for transplantation, cells were collected, spun down, washed with Ca$^{2+}$/Mg$^{2+}$-free HBSS and resuspended to a final concentration of 10$^5$ cells/μl in Ca$^{2+}$/Mg$^{2+}$-free HBSS.

Transplantation:

R6/2×rag1$^{-/-}$ and rag1$^{-/-}$ littermates were transplanted within 24 hours of birth, postnatal day 1 ("P1"). The mice were anesthetized by deep hypothermia and transplanted either bilaterally in the striatum with a total of 100,000 cells (2-point transplantation paradigm) as described (Windrem et al., "Neonatal Chimerization with Human Glial Progenitor Cells can Both Remyelinate and Rescue the Otherwise Lethally Hypomyelinated Shiverer Mouse," *Cell Stem Cell* 2:553-565 (2008), which is hereby incorporated by reference in its entirety). The cell transplant procedures were conducted under aseptic conditions.

Histology:

Animals were sacrificed using sodium pentobarbital and perfused transcardially with saline followed by 4% paraformaldehyde, and their brains were processed for immunocytochemistry as previously described. Sagittal equidistant cryosections of sections (20 μm) spanning the whole brain were analyzed. Human cells were identified through immunostaining with anti-human nuclear antigen ("hNA") antigen (1:800, MAB1281, Millipore, Temecula, Calif., USA). Engrafted human cells were mapped using Metamorph imaging software and an automated fluorescence microscope (Leica Microsystems, Wetzlar, Germany). Brain sections were then co-stained to define phenotype, using combinations of the following antibodies: Mouse anti-huntingtin antibody clone EM48 (1:250, MAB5374, Millipore), mouse anti-glial fibrillary acidic protein (GFAP) (1:800, SMI-21, Covance, Princeton, N.J., USA); Dilution) Rabbit anti-Olig2 (1:400, RA25081 Neuromics, Edina, Minn., USA), Rabbit anti-PDGFRα (1:400, 5241 Cell Signaling Technology, Danvers, Mass., USA). Slides were analyzed serially every 24th section using the optical fractionator method to estimate the total number of engrafted human cells of each histological marker (GFAP, Olig2, PDGFRα) using StereoInvestigator imaging software (MicroBrightField, Burlington, Vt., USA).

Behavioral Assessment:

Mice from different litters were randomly assigned for rotarod evaluation. The mice were handled under the same conditions by one investigator at the same day and time. The female (Sorge et al., "Olfactory Exposure to Males, Including Men, Causes Stress and Related Analgesia in Rodents,". *Nature Methods* 11: 629-632 (2014), which is hereby incorporated by reference in its entirety) experimenter was blind as to the genotype and treatment of the mice. The mice were tested every four weeks, in 3 rotarod trials per session, allowing at least 5 minutes of rest between each trial. The rotarod (Ugo Basile) accelerated from 5 to 40 rpm and each trial lasted 5 minutes. The three values were averaged, and the data were analyzed using 2-way ANOVA (treatment× genotype) and linear regression analysis, using GraphPad Prims v.5.0b (GraphPad, Sand Diego, Calif.).

Survival:

Mice from multiple litters were assigned to the experiment. The mice were kept in mix genotype with 3 to 5 mice per cage. In order to determine lifespan, the mice were checked once a day at a younger age. Diseased mice were checked twice a day. The criterion for euthanasia was determined at the point in time when R6/2 mice were found moribund and could no longer right themselves after 30 seconds when placed on their side. Deaths that occurred overnight were recorded the following morning.

Statistics:

Statistical analyses and graphs were generated using GraphPad Prism v.5.0b (GraphPad Software, San Diego, USA). All the results are expressed as mean±standard error (SEM). Comparisons between several groups were performed using ANOVA with Bonferroni post hoc analysis. Significance was defined as $p \leq 0.05$.

Electrophysiological Recordings:

Mice at 12 weeks after birth were deeply anaesthetized with ketamine (100 mg/kg) and xylazine (10 mg/kg). An open window on the top of the mouse skull was cut and the brain was removed rapidly into the oxygenated, ice-cold, cutting solution, then glued to the stage of a Leica VT1000S vibratome (Leica Biosystems, Buffalo Grove, Ill., USA), with the posterior surfaces down. Transverse brain slices of 300 μm were cut in the oxygenated, ice-cold, cutting solution containing (in mM): 2.5 KCl, 1.25 NaH2PO4, 10 MgSO4, 0.5 CaCl2, 10 glucose, 26 NaHCO3 and 230 sucrose. Slices containing the striatum were incubated in the slice solution gassed with 5% $CO_2$ and 95% $O_2$ for at least 1 h, before being placed in a recording chamber (1.5 ml), which was superfused with the slice solution gassed with 5% $CO_2$/95% $O_2$ at room temperature (23-24° C.). The slice solution (ACSF) contained (in mM): 126 NaCl, 26 NaHCO3, 2.5 KCl, 1.25 NaH2PO4, 2 MgSO4, 2 CaCl2, 10 lactate, and 10 glucose.

The recording chamber was placed on the stage of an Olympus BX51 upright microscope (Olympus Optical Co., NY, USA) equipped with DIC optics, and cells were visualized with a 60× water immersion lens. Patch electrodes with a resistance of 7-9 MΩ) were pulled from TW150E-4 glass capillaries (i.d. 1.12 mm, o.d. 1.5 mm, World Precision Instruments, USA) using a PC-10 electrode puller (Narishige International USA, Inc. East Meadow, N.Y., USA). For normal hGPC-engrafted R6/2 mice, striatal MSNs were identified morphologically under DIC optics, while in Q23 vs. Q73 mHtt+ hGPC-chimeric striata, MSNs were identified in the vicinity of mHtt:EGFP-expressing glia under two-photon microscopy. In both cases all neurons were patched with the patch pipette filled with the pipette solution (mM): 140 potassium gluconate, 2 MgCl2, 10 HEPES, 4 Mg-ATP, 0.3 Na-GTP, and 5 sodium phosphocreatine (pH 7.3). A seal resistance <5 GΩ was rejected.

Membrane currents and potentials were recorded under the voltage-clamp and current-clamp configurations, respectively, with Axopatch MultiClamp (Axon Instruments, Forster City, Calif., USA), interfaced to a desktop IBM compatible computer via a Digidata A/D converter digitizer 1440A (Axon Instruments, Forster City, Calif., USA). Recording signals were filtered through a low-pass filter with a 2 kHz cut-off frequency and sampled by the pCLAMP 10.2 software (Axon Instruments Inc.) with an interval of 50 μs.

Interstitial Potassium Recordings:

In vivo recordings were obtained from the cortex and striatum of 12-18 week-old R6/2 HD mice and wild-type littermates, as well as from their matched littermates transplanted neonatally with a total of $2 \times 10^5$ CD44-sorted human GPCs, with bilateral injections of $5 \times 10^4$ cells each into striatum and the parietal cortical mantle. Mice were anesthetized using isoflurane (1.5% mixed with 1-2 L/min $O_2$), and their heads restrained with a custom mini-frame, to which the mice were habituated the day before in multiple sessions, with a total training duration of 2 hr. On the day of recording, a 3 mm craniotomy was opened over the motor cortex (centered at 1.5 mm lateral to bregma), and the dura removed. The procedure lasted <20 min to minimize anesthesia exposure during recording, and 30 minute recovery from isofluorane anesthesia was allowed post-operatively. Body temperature was maintained throughout with a heating pad. The aCSF solution contained (in mM) 126 NaCl, 2.5 KCl, 1.25 $NaH_2PO_4$, 2 $MgCl_2$, 2 $CaCl_2$, 10 glucose, and 26 $NaHCO_3$, pH 7.4.

Ion-sensitive microelectrodes ("ISM") for $K^+$ recording were prepared as glass pipettes (WPI, TW150-4) with a tip diameter of 1-3 μm, as previously described (Wang et al., "Astrocytes Modulate Neural Network Activity by $Ca(2)+$—Dependent Uptake of Extracellular $K^+$," *Sci Signal.* 5 (218): ra26 (2012) and Wang et al., "Bergmann Glia Modulate Cerebellar Purkinje Cell Bistability via $Ca^{2+}$-Dependent $K^+$ Uptake," *Proc Natl Acad Sci USA* 109 (20):7911-6 (2012), which are hereby incorporated by reference in their entirety). The pipettes were silanized with dimethylsilane I (Fluka, Sigma) and filled with $K^+$ ionophore I cocktail B (Fluka). The backfill solution for $K^+$ ion specific meter (Hanna Instruments, Woonsocket, R.I.) was 0.15 M KCl. All $K^+$ electrodes were calibrated before and after each experiment and the calibration data were fitted to the Nikolsky equation to determine electrode slope and interference (Wang et al, "Induction of Immune Tolerance in Mice with a Novel Mucosal Nanoemulsion Adjuvant and Self-Antigen," Nanomedicine 7 (6):867-76 (2012), which is hereby incorporated by reference in its entirety). The $K^+$ electrodes were inserted vertically into the brain within the craniotomy site, at 2.0 mm lateral to bregma, at depths of 600 μm and 2.2 mm for the cortex and striatum, respectively. Mean values over 20-30 minute recording periods were utilized.

Example 1—Glial Progenitors and Astrocytes were Generated from hES Cells Expressing Mutant Htt Applicants previously developed a high-efficiency protocol for generating GPCs and their derived astroglia and oligodendrocytes from both hESCs and induced pluripotential cells ("hiPSCs") (Wang et al., "Human iPSC-Derived Oligodendrocyte Progenitor Cells can Myelinate and Rescue a Mouse Model of Congenital Hypomyelination," *Cell Stem Cell* 12:252-264 (2013), which is hereby incorporated by reference in its entirety). Neonatal engraftment of these cells into immunodeficient mice yields human glial chimeric mice, in which substantially all GPCs and a large proportion of astrocytes are of patient-specific, human donor origin. Using this approach, applicants first sought to generate GPCs from huntingtin mutant pluripotential cells, and to then establish human glial chimeras with those cells, as a means of assessing the specific effects of human huntingtin mutant glia on striatal function.

To that end, huntingtin mutant hESCs, the GENEA 20 line bearing a 48 CAG repeat expansion in the first exon of the HTT gene, as well as its matched sibling control, GENEA 19, which has a normal 18 CAG repeat length in exon 1 were utilized (Bradley et al., "Derivation of Huntington's Disease-Affected Human Embryonic Stem Cell Lines," *Stem Cells Dev.* 20 (3): 495-502 (2011), which is hereby incorporated by reference in its entirety). These lines were derived from blastocysts produced from the same parents, and were thus fraternal twins except for their different CAG repeat lengths in exon 1. GPCs were then induced from the GENEA 19 and GENEA 20 hES lines, using a previously described protocol (Wang et al., "Human iPSC-Derived Oligodendrocyte Progenitor Cells can Myelinate and Rescue a Mouse Model of Congenital Hypomyelination," *Cell Stem Cell* 12:252-264 (2013), which is hereby incorporated by reference in its entirety). When harvested after an average in vitro propagation of 200 days of glial induction (range: of 160-240), an average of 56.0±4.6% of normal (GENEA 19) and 45.8±7.0% of huntingtin mutant (GENEA 20) cells expressed the bipotential astrocyte-oligodendrocyte progenitor marker PDGFaR/CD140a (Sim et al., "CD140a Identifies a Population of Highly Myelinogenic, Migration-Competent and Efficiently Engrafting Human Oligodendrocyte Progenitor Cells," *Nat Biotechnol* 29 (10): 934-941 (2011), which is hereby incorporated by reference in its entirety). The remainder were almost entirely CD44$^+$/CD140a$^-$ cells, which typify astroglia and their progenitors (Liu et al., "CD44 Expression Identifies Astrocyte-Restricted Precursor Cells," *Dev Biol.* 276 (1): 31-46 (2004), which is hereby incorporated by reference in its entirety). Immunostaining revealed that <1% of cells expressed either the neuronal antigens HuC/D or MAP2, and pluripotency-associated gene expression was undetectable by either immunocytochemistry or qPCR. Thus, the grafted cell populations were comprised almost entirely of CD44-defined astroglial progenitors and bipotential oligodendrocyte-astrocyte GPCs. The GENEA 20- and GENEA 19-derived glia were neonatally engrafted bilaterally into the neostriata of rag1$^{-/-}$ immunodeficient mice (n=38 and 35, respectively), to establish mutant huntingtin (mHtt) human glial chimeras and their normal human glial controls.

Example 2—Chimerization Yielded the Substantial Replacement of Striatal Glia by mHtt$^+$ Human Glia Upon weaning, human glial chimeric mice were randomly assigned to matched groups for either serial analysis of their motor performance by rotarod, or for serial sacrifice for histological analysis as a function of age. Histological analysis revealed that the striata of these mice rapidly and efficiently engrafted with donor hESC-derived hGPCs (FIGS. 1A-1B). The donor cells first expanded to pervade the host striata as persistent hGPCs, in part replacing the resident murine GPCs in the process (FIGS. 1C-1F). A fraction of the donor cells then differentiated as astroglia, especially so in striatal white matter tracts. Fibrous astrocytes appeared early, and were arrayed densely within striatal white matter tracts by 6-8 weeks after neonatal graft, whereas striatal protoplasmic astrocytes appeared later and were first apparent in significant numbers only by 12 weeks (FIGS. 1G-1H). Over the weeks thereafter, the host striatal hGPCs were substantially replaced by human donor cells, whether by HD hESC-derived hGPCs or their normal sibling-derived control hGPCs; in each case, hGPCs were typically the dominant population by 20 weeks, and few if any murine GPCs remained in any of the engrafted striata after 40 weeks (FIGS. 1C-1D). Transplanted cells did not differentiate into neurons, as evidenced by their lack of expression of either MAP2 or NeuN, two distinct markers of mature neuronal phenotype. No evidence of tumor formation or aberrant differentiation of hESC-derived GPCs was noted in any of the mice.

Example 3—Motor Performance was Impaired in mHtt Glial Chimeras

Figure 2:
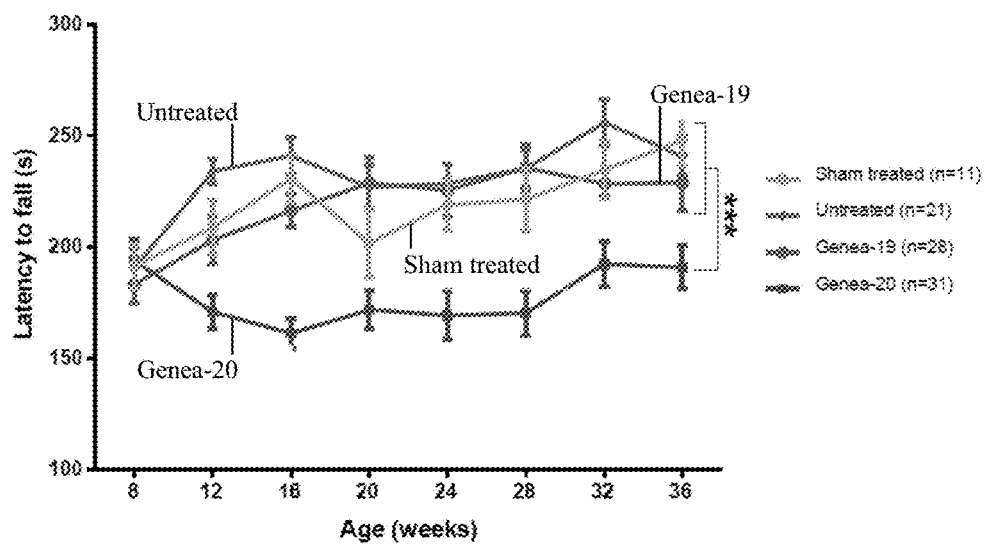
FIG. 2 shows that HD ESC-derived glial chimeras exhibit slow motor learning. Mice engrafted with GENEA 20-derived glia expressing mHtt demonstrated significantly slowed motor learning compared to littermates chimerized with GENEA 19-derived normal HTT GPCs or control mice (sham-treated or untreated). In particular, the mHtt glial chimeras (GENEA 20) manifested significant age-dependent decrements in motor coordination relative to their normal HTT (Genea G19) hESC GPC-derived chimeric controls. These differences appeared to reflect the relative lack of age-dependent improvement in rotarod performance by the mHTT GPC GPC-engrafted mice, suggesting a glial-mediated deficit in motor learning.

Among the 109 mice assigned to rotarod assessment of motor performance, those chimeric for HD hESC (GENEA 20)-derived glia manifested significantly slowed motor learning compared to littermates chimerized with normal Htt GPCs (GENEA 19). In particular, the GENEA 20-derived mHtt glial chimeras manifested significant decrements in motor coordination relative to four independent control groups, which included: 1) GENEA19 GPC-derived chimeric controls; 2) murine GPC-engrafted controls; 3) uninjected controls; and 4) saline-injected controls (p<0.001 by 2-way ANOVA; F (7, 717)=5.925) (FIG. 2).

Figures 8A, 8B, 8C, 8D, 8E, 8F:
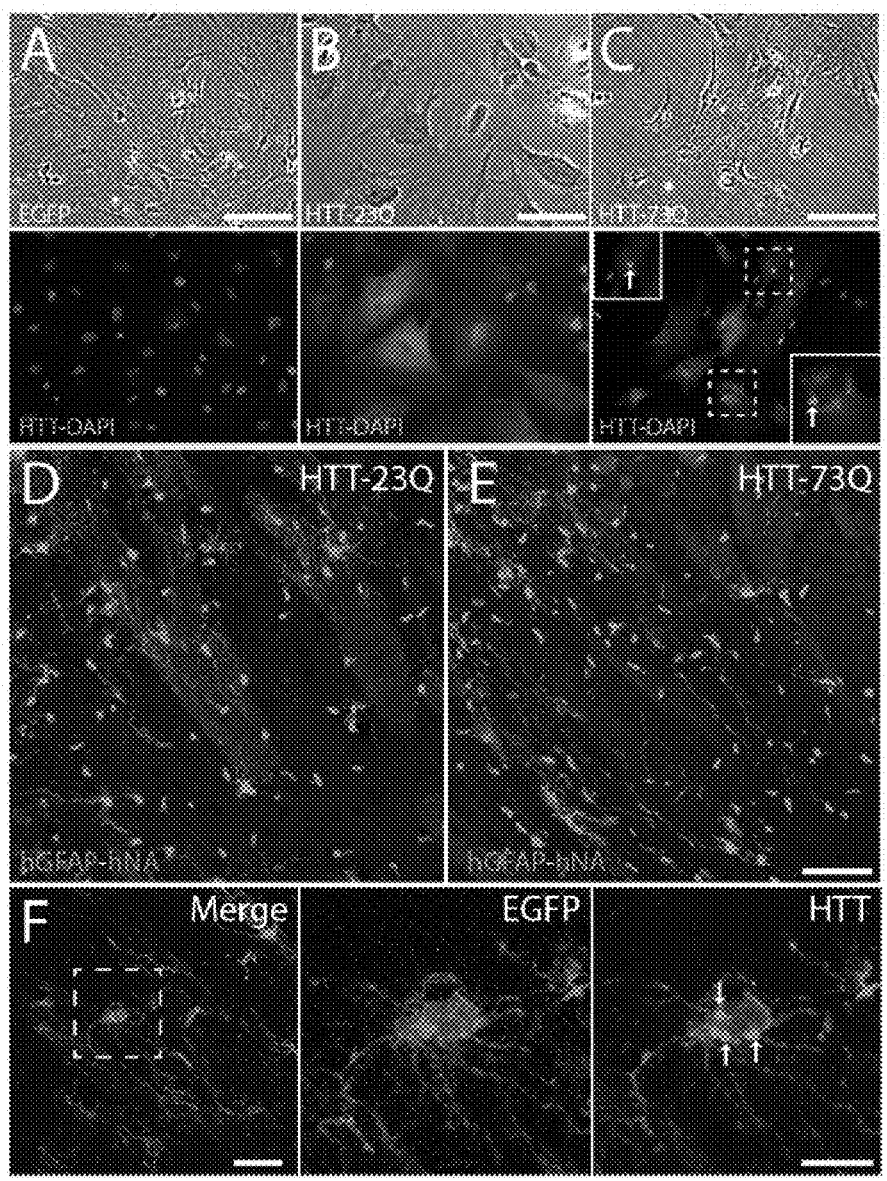
FIGS. 8A-8F illustrate the dense engraftment of the recorded striata within human donor cells, in both the Q23 and Q73 mHtt hGPC-engrafted striata.

Example 4—Normal Medium Spiny Neurons were Hyperexcitable in the Presence of mHtt$^+$ Glia To better understand the physiological basis for the relatively impaired motor performance of mHtt glial-engrafted mice, whether chimerization with mHTT glia influenced the physiology of medium spiny neurons was investigated. To that end, striatal glial chimeras were established in otherwise wild-type immunodeficient mice, via neonatal intrastriatal injection of mHtt-expressing human fetal glia. For this purpose, mHtt-transduced fetal tissue-derived hGPCs rather than HD hESC-derived GPCs was used, so as to assess the effects of mutant Htt bearing longer CAG repeats than the 48Q mHtt expressed by GENEA 20-derived hGPCs. It was postulated that longer CAG repeat expansions would accelerate glial pathology, and thus potentiate detection of paracrine neuronal dysfunction at the relatively young ages and compressed experimental time frames used in this study. To that end, hGPCs were isolated from 18-20 week human fetal forebrain, using immunomagnetic sorting directed against CD44, a hyaluronic acid receptor ectodomain selectively expressed by astrocyte-biased glial progenitor cells (Liu et al., "CD44 Expression Identifies Astrocyte-Restricted Precursor Cells," *Dev Biol.* 276 (1): 31-46 (2004), which is hereby incorporated by reference in its entirety). Cells were then transduced with a lentiviral vector encoding the first exon of the HTT gene bearing either mutant (73Q) or normal (23Q) huntingtin, each upstream to an EGFP reporter, and then injected the transduced cells into the striata of neonatal rag1$^{-/-}$ immune deficient mice. The mice were sacrificed 12 weeks later and striatal slices were prepared; human GFP$^+$ glial-rich regions were imaged by 2-photon microscopy, and their resident striatal neurons patch clamped using previously described methods (Benraiss et al., "Sustained Mobilization of Endogenous Neural Progenitors Delays Disease Progression in a Transgenic Model of Huntington's Disease," *Cell Stem Cell* 12:787-799 (2013), which is hereby incorporated by reference in its entirety). Subsequent histology and immunolabeling confirmed the dense engraftment of the recorded striata with human donor cells, in both the Q23 and Q73 mHtt hGPC-engrafted striata, whose extents of donor cell engraftment were indistinguishable at the 12 week time-point at which recordings were obtained (FIG. 8). Of note, whereas the distributions of Q23 and Q73 mHtt-transduced glia did not differ in engrafted chimeras, the Q73 mHtt glia could be recognized by cytoplasmic Htt aggregates, in vivo as well as in culture, while the Q23-transduced controls exhibited no such aggregate formation (FIG. 8).

Physiologically, neurons in striata engrafted with 73Q mHtt glia manifested significantly higher input resistance relative to those engrafted with either 23Q mHtt- or EGFP-only transduced control glia, and required significantly fewer current injections to fire action potentials relative to control glia-engrafted mice (FIGS. 3A-3D). The higher input resistance of these neurons was manifest in their current-voltage and current-resistance curves as well (FIGS. 3E-3F), and suggested the significant relative hyperexcitability of striatal neurons in a mutant Htt-glial environment. Interestingly, despite their hyperexcitability in response to current injection, striatal neurons within 73Q glial chimeric striata manifested a significantly lower frequency of spontaneous EPSPs than did striatal neurons in all control groups (FIGS. 3F-3G), suggesting a deleterious effect of mHtt glial chimerization on synaptic input to resident MSNs within the recipient striatum.

Figures 4A, 4B, 4C, 4D, 4E, 4F, 4G, 4H:
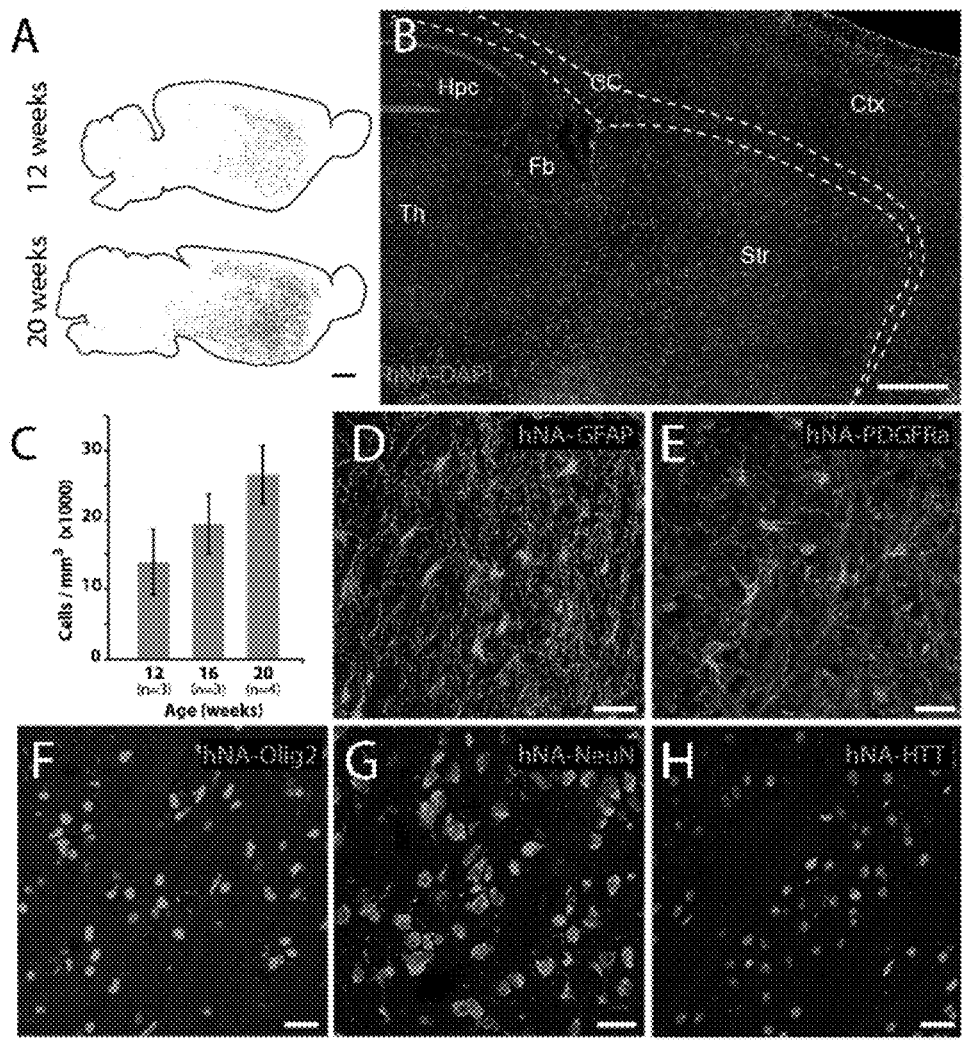
FIGS. 4A-4H show that CD44-sorted hGPCs colonized and replaced endogenous glia within the R6/2×rag1$^{-/-}$ striatum. Striatal engraftment of the R6/2 mice by CD44-sorted hGPCs was robust and dense.
Figures 9A, 9B, 9C, 9D, 9E:
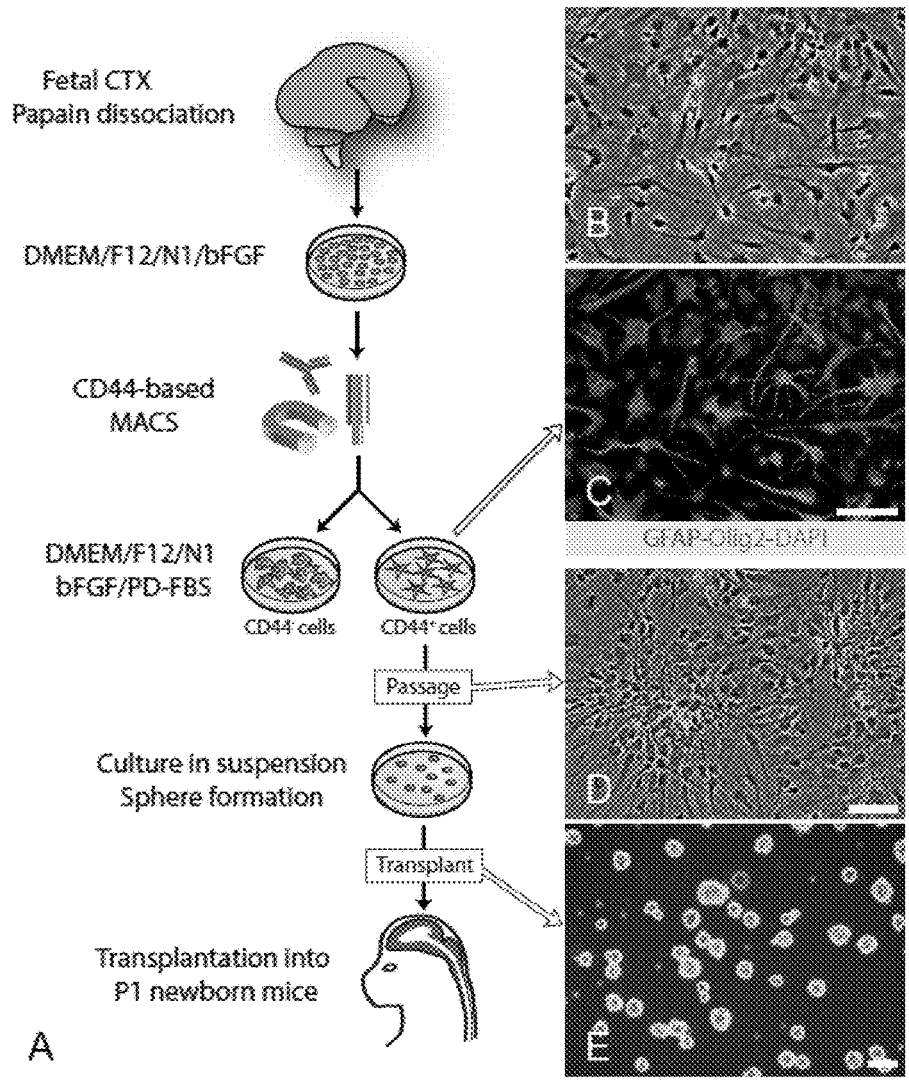
FIGS. 9A-9E exhibits the morphology and antigenicity of hGPCs derived from 18-22 wk gestational age human fetal forebrain.

Example 5—Chimerization with Normal Glia Slows Disease and Extends Survival of R6/2 Mice Since engraftment of normal striata with mutant Htt-expressing GPCs impaired striatal neuronal function and physiology, whether the reverse might be true, i.e., if neonatal engraftment of the HD striata with normal glia might rescue aspects of HD phenotype, was investigated. To this end, normal human GPCs were engrafted into the striata of newborn R6/2 (120 CAG) mice (Mangiarini et al., "Exon 1 of the HD Gene with an Expanded CAG Repeat is Sufficient to Cause a Progressive Neurological Phenotype in Transgenic Mice," Cell 87:493-506 (1996), which is hereby incorporated by reference in its entirety), which transgenically express a mutant exon 1 of the HTT gene, and typically die by 16 weeks of age. For this experiment, astrocyte-biased GPCs were isolated from 18-22 week g.a. fetal human brain using magnetic activated cell sorting ("MACS") targeting CD44, as noted above (FIG. 9A) (Liu et al., "CD44 Expression Identifies Astrocyte-Restricted Precursor Cells," Developmental Biol. 276:31-46 (2004), which is hereby incorporated by reference in its entirety). The CD44-sorted cells were then transplanted into the striata of the newborn R6/2 mice, using an injection protocol previously described for use in neonatal callosal injection (Windrem et al., "Fetal and Adult Human Oligodendrocyte Progenitor Cell Isolates Myelinate the Congenitally Dysmyelinated Brain," Nat. Med. 10:93-97 (2004), which is hereby incorporated by reference in its entirety) (FIGS. 9B-9E), but instead targeting the striata. Striatal engraftment of the R6/2 mice by CD44-sorted hGPCs was robust (FIGS. 4A-4B), and achieved densities of >15,000 human cells/mm$^3$ by 16 weeks of age (FIG. 4C). The CD44-sorted cells integrated as both astrocytes (FIG. 4D) and as persistent GPCs (FIGS. 4E-F), but not as neurons (FIG. 4G). Importantly, the integrated human cells did not manifest detectable HTT aggregates; the staining patterns of HTT and human nuclear antigen were always entirely non-overlapping (FIG. 4H). As such, there was no evidence of HTT transmission from hst to donor cells over the time frame studied.

Figures 5A, 5B:
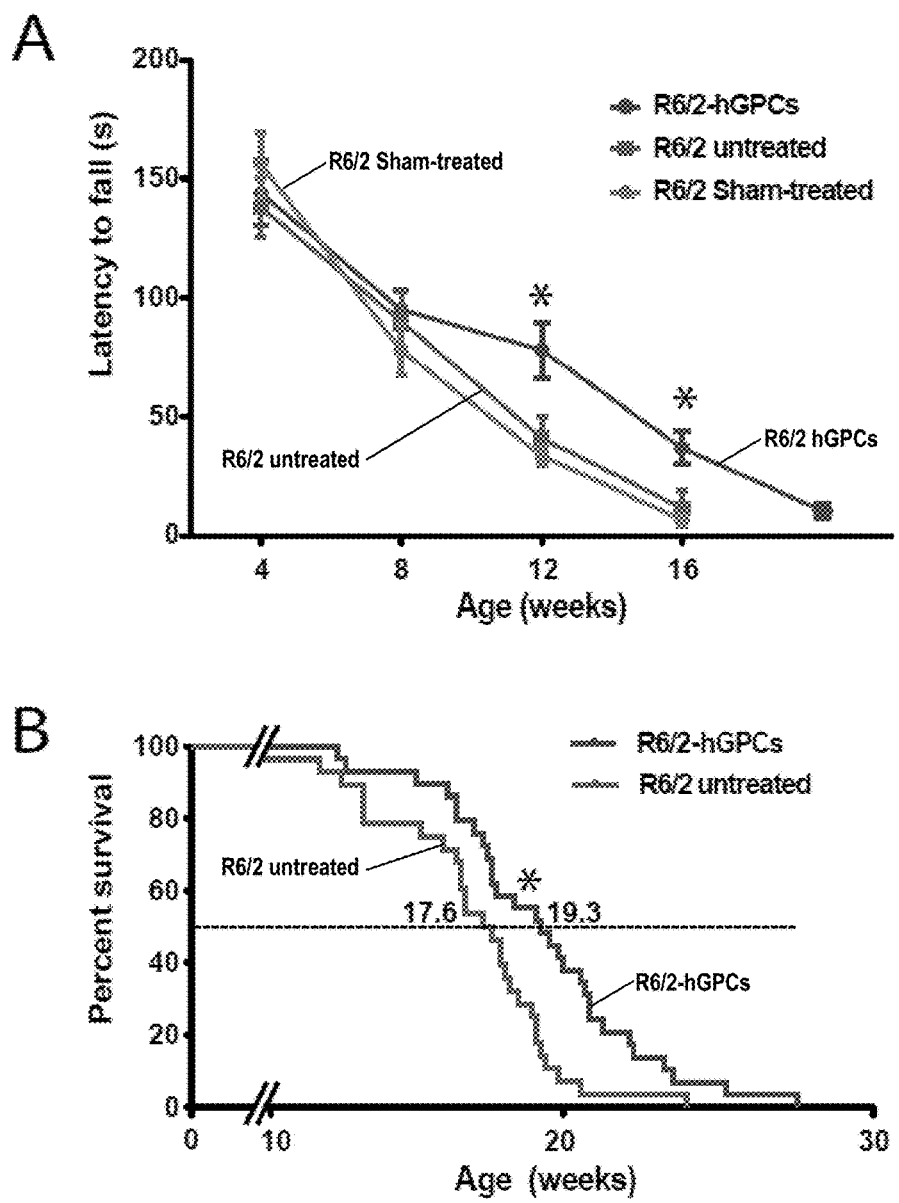
FIGS. 5A-5B show that chimerization with normal glial slows motor loss and extends survival of R6/2 mice.

The hGPC-engrafted chimeric R6/2 mice displayed significantly slower motor deterioration than did their untreated controls, as assessed by their performance upon a constantly accelerating rotarod. Linear regression revealed that the rate of motor deterioration was significantly slowed in the human GPC engrafted mice, relative to untreated controls (F=4.8 [2, 124 d.f.]; P<0.001) (FIG. 5A).

On that basis, whether the performance enhancement associated with engraftment by normal glia might be sufficient to influence the survival of R6/2 (120 CAG) mice was investigated. R6/2 (120Q)×rag1$^{-/-}$ mice whose striata were neonatally transplanted with normal human glia survived significantly longer than unengrafted mice, with a mean increase in lifespan of 12 days (hGPC-engrafted, n=29; untreated, n=28; P<0.01, Mantel-Cox Log-rank test) (FIG. 5B).

Example 6—R6/2 MSN Physiology was Altered in the Presence of Normal Glia

To assess the potential physiological basis for the relatively improved function and survival of R6/2 mice engrafted with human glia, whether chimerization with normal glia influenced the physiology of resident R6/2 striatal neurons was next investigated. This experiment, which assessed the effects of a normalized glial environment on HD MSNs, provided a corollary to applicants prior assessment, in which normal MSNs were evaluated in an HD glial environment. To this end, 19 neonatal immunodeficient rag1$^{-/-}$×R6/2 (120 CAG) mice were either engrafted (n=8) or not (n=11) with CD44-sorted hGPCs; 12 weeks later, they were sacrificed, slice preparations were taken, and MSNs were patch-clamped. In addition, 18 wild-type× rag1$^{-/-}$ mice were similarly assessed, 7 of which had been neonatally engrafted with CD44-sorted hGPCs, and 11 of which were unengrafted controls. Successful engraftment of the recorded striata by human donor cells was verified histologically after recording. Mice that displayed poor engraftment, defined as <1000 human nuclear antigen+ cells/mm$^3$, were removed from the study (vs. an average of >10,000 cells/mm$^3$ in successful grafts; see Tables 1-2).

TABLE 1

| | | | | | hESC-derived GPCs into wild-type rag1 immunodeficients |
|---|---|---|---|---|---|
| Mean ± SEM | | % GFAP$^+$ | % olig2$^+$ | Total cells | hNA$^+$/mm$^3$ striatum |
| GENEA19 (18Q) | 20 weeks (n = 3) | 2.1 ± 0.6 | 71.8 ± 19.4 | 74,173 ± 14,305 | 21,000 ± 3,608 |
| | 40 weeks (n = 4) | 1.66 ± 0.5 | 82.51 ± 8.6 | 42,807 ± 6,991 | 9,335 ± 1,341 |

TABLE 1-continued hESC-derived GPCs into wild-type rag1 immunodeficients

| Mean ± SEM | | % GFAP+ | % olig2+ | Total cells | hNA+/mm³ striatum |
|---|---|---|---|---|---|
| GENEA20 (48Q) | 20 weeks (n = 3) | 2.3 ± 0.4 | 56.4 ± 7.5 | 42,520 ± 8,792 | 10,843 ± 3,323 |
| | 40 weeks (n = 4) | 2.2 ± 0.7 | 72.7 ± 6.3 | 80,798 ± 7,131 | 16,126 ± 380 |

TABLE 2

CD44+ GPCs into R6/2 × rag1−/− mice

| Survival time | % GFAP+ | % olig2+ | Total cells | hNA+/mm³ striatum |
|---|---|---|---|---|
| 20 weeks (n = 4) | 1.71 ± 0.3 | 45.23 ± 7.8 | 77,756 ± 21,000 | 16,651 ± 3,694 |

Figures 6A, 6B, 6C, 6D, 6E, 6F:
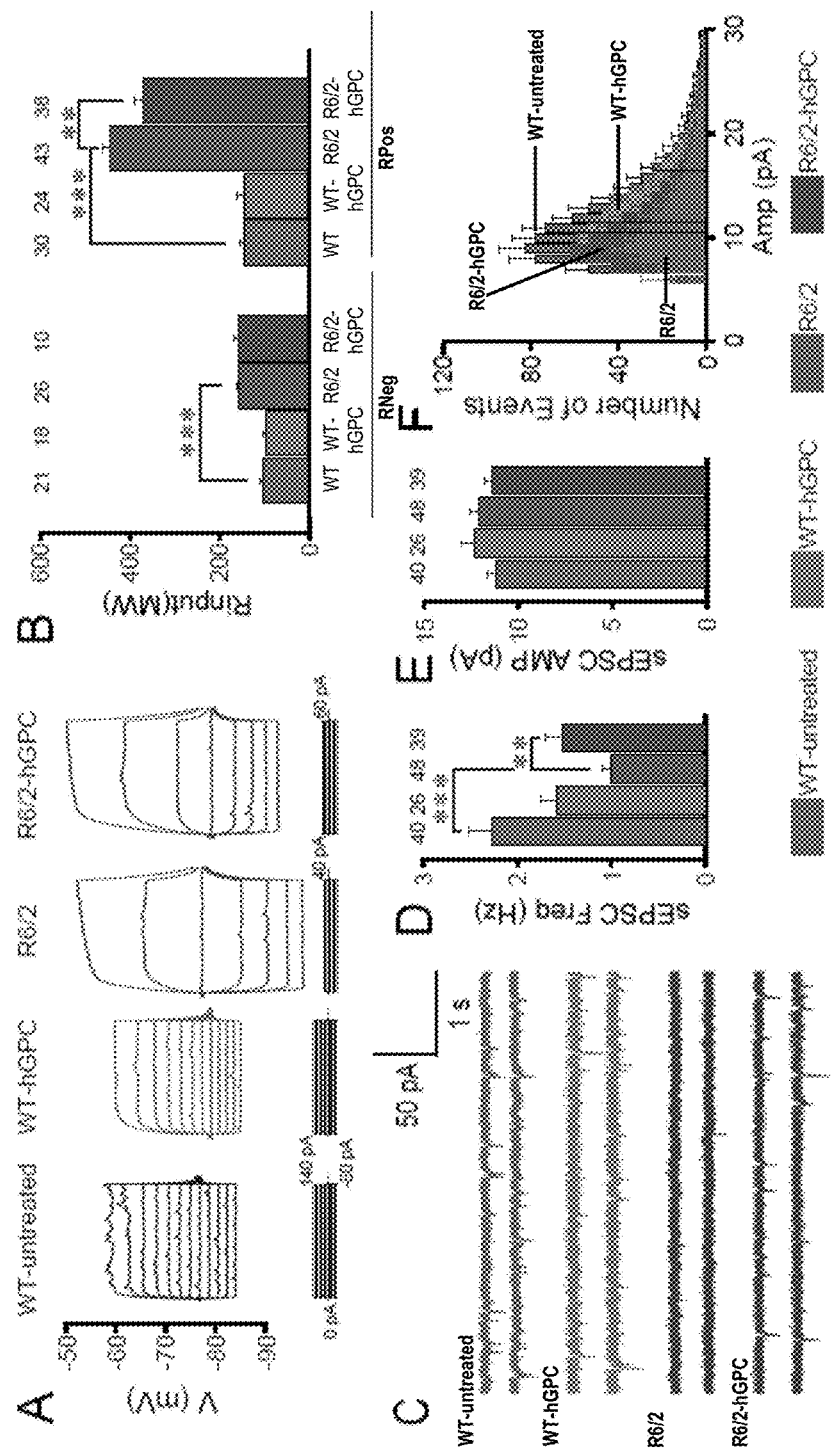
FIGS. 6A-6F shows that chimerization with normal glia partially normalizes MSN physiological function.

Abbreviations: GPC, glial progenitor cell; GFAP, glial fibrillary acidic protein; hNA, human nuclear antigen The input resistance ("$R_{input}$") of R6/2 striatal neurons was significantly higher than that of their wild-type controls, as has been previously reported (Ariano et al., Striatal Potassium Channel Dysfunction in Huntington's Disease Transgenic Mice," *J Neurophysiol.* 93 (5): 2565-2574 (2005) and Klapstein et al., "Electrophysiological and Morphological Changes in Striatal Spiny Neurons in R6/2 Huntington's Disease Transgenic Mice," *J Neurophysiol.* 86 (6): 2667-2677 (2001), which are hereby incorporated by reference in their entirety). Significantly though, it was found that the $R_{input}$ of R6/2 neurons was lower in the presence of engrafted normal human CD44-derived glia (FIGS. 6A-6B). Similarly, whereas the spontaneous EPSP frequency was significantly lower in R6/2×rag1−/− striatal neurons than in rag1−/− wild-type controls, the EPSP frequency of CD44-engrafted R6/2s was restored to levels not significantly different from those wild-type controls (FIGS. 6C-6D). While the EPSP amplitude of R6/2 striatal neurons was unaffected by chimerization (FIG. 6E), the lower frequency of sEPSPs in the R6/2 MSNs, and their partial restoration by engrafted normal glia, was consistent across the spectrum of EPSP amplitudes (FIG. 6F). Of note, engraftment with normal CD44-defined glia had no effect on any electrophysiological measure in otherwise normal rag1−/− wild-type mice; only in R6/2 mice did glial engraftment affect input resistance and spontaneous EPSP frequency.

Figures 3A, 3B, 3C, 3D, 3E, 3F, 3G, 3H:
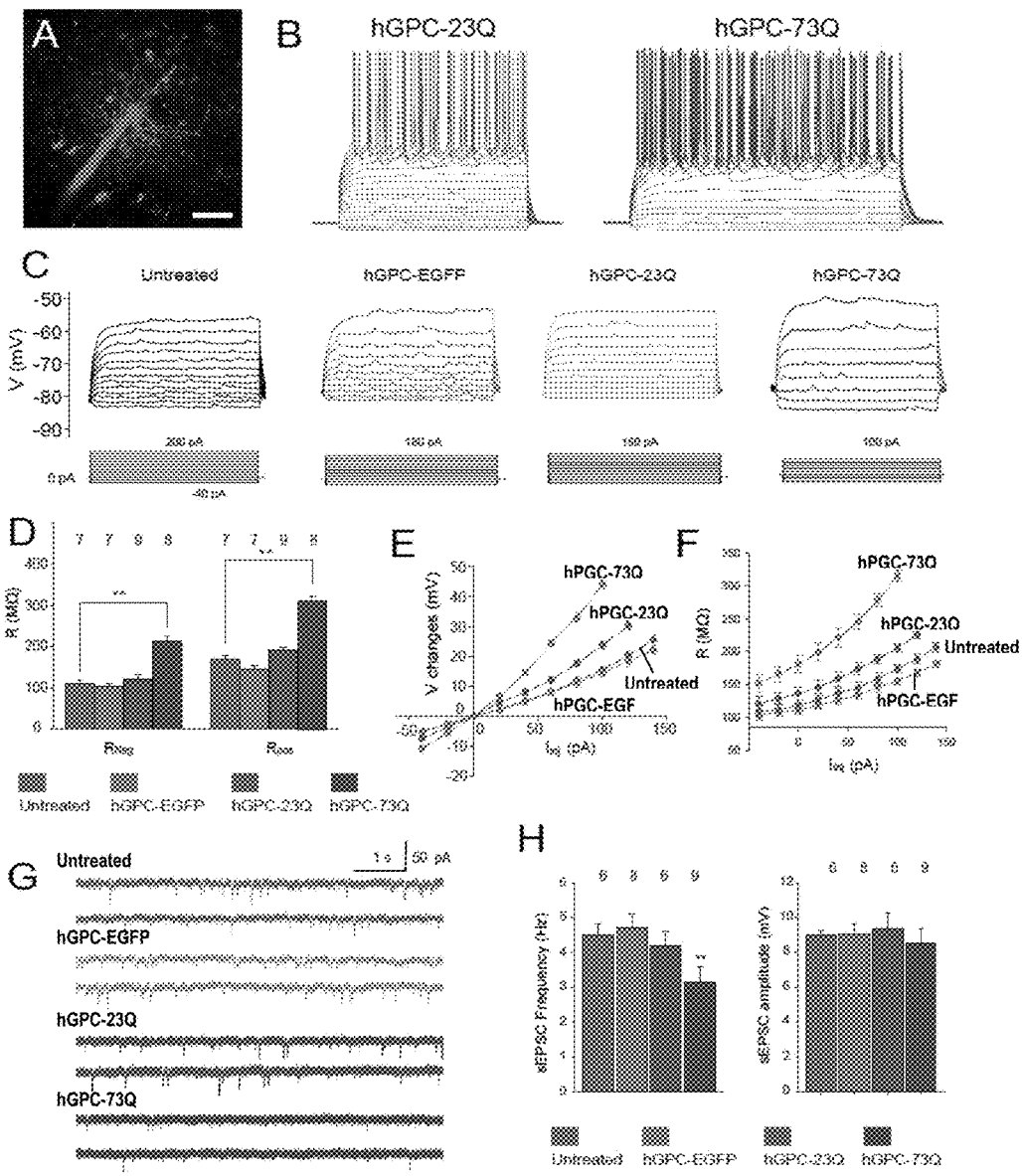
FIGS. 3A-3H show that striatal neurons are hyperexcitable in mice chimerized with mHTT-transduced hAPCs. Human glial chimeric striata were established with fetal human glia transduced to overexpress mHtt.

Example 7—Normal Glial Engraftment Reduced Otherwise Excessive Interstitial K+ Levels in the HD Brain A number of studies have implicated dysfunction of neuronal potassium channels in the HD striatum (Ariano et al., Striatal Potassium Channel Dysfunction in Huntington's Disease Transgenic Mice," *J Neurophysiol.* 93 (5): 2565-2574 (2005) and Klapstein et al., "Electrophysiological and Morphological Changes in Striatal Spiny Neurons in R6/2 Huntington's Disease Transgenic Mice," *J Neurophysiol.* 86 (6): 2667-2677 (2001), which are hereby incorporated by reference in their entirety), and a recent study has highlighted the contribution of defective glial potassium uptake to HD pathogenesis (Tong et al., "Astrocyte Kir4.1 Ion Channel Deficits Contribute to Neuronal Dysfunction in Huntington's Disease Model Mice," *Nat Neurosci* 17 (5): 694-703 (2014), which is hereby incorporated by reference in its entirety). Astrocytes play an important role in buffering K+ released during synaptic transmission (Djukic et al., "Conditional Knock-Out of Kir4.1 Leads to Glial Membrane Depolarization, Inhibition of Potassium and Glutamate Uptake, and Enhanced Short-Term Synaptic Potentiation," *J Neurosci.* 27 (42): 11354-11365 (2007); Ballanyi et al., "Ion Activities and Potassium Uptake Mechanisms of Glial Cells in Guinea-Pig Olfactory Cortex Slices," *Journal of physiol.* 382: 159-174 (1987); and Larsen et al., "Contributions of the Na(+)/K(+)-ATPase, NKCC1, and Kir4.1 to Hippocampal K(+) Clearance and Volume Responses," *Glia* 62 (4): 608-622 (2014), which are hereby incorporated by reference in their entirety). If astrocyte K+ uptake is impaired, then ineterstitial K+ rises, and the transmembrane gradient for K+ is decreased, resulting in the relative depolarization, and hence increased excitability, of local neurons (Djukic et al., "Conditional Knock-Out of Kir4.1 Leads to Glial Membrane Depolarization, Inhibition of Potassium and Glutamate Uptake, and Enhanced Short-Term Synaptic Potentiation," *J Neurosci.* 27 (42): 11354-11365 (2007) and Wang et al., "Astrocytes Modulate Neural Network Activity by Ca(2)+-Dependent Uptake of Extracellular K+. *Sci Signal.* 5(218): ra26 (2012), which are hereby incorporated by reference in their entirety). The observation of the increased membrane resistance of wild-type MSNs in mHtt (73Q) glial chimeras suggested precisely such a defect in potassium handling by mHtt-expressing human glia (FIGS. 3D-3F). On that basis, potassium microelectrodes were next used to ask whether the hyperexcitability and increased membrane resistance of R6/2 striatal neurons was associated with elevated interstitial K+ in vivo. This was found to be the case (FIG. 7), in that the levels of interstitial K+ were significantly higher in R6/2 mice than their wild-type littermates, at both 12 and 16 weeks of age.

Figure 7:
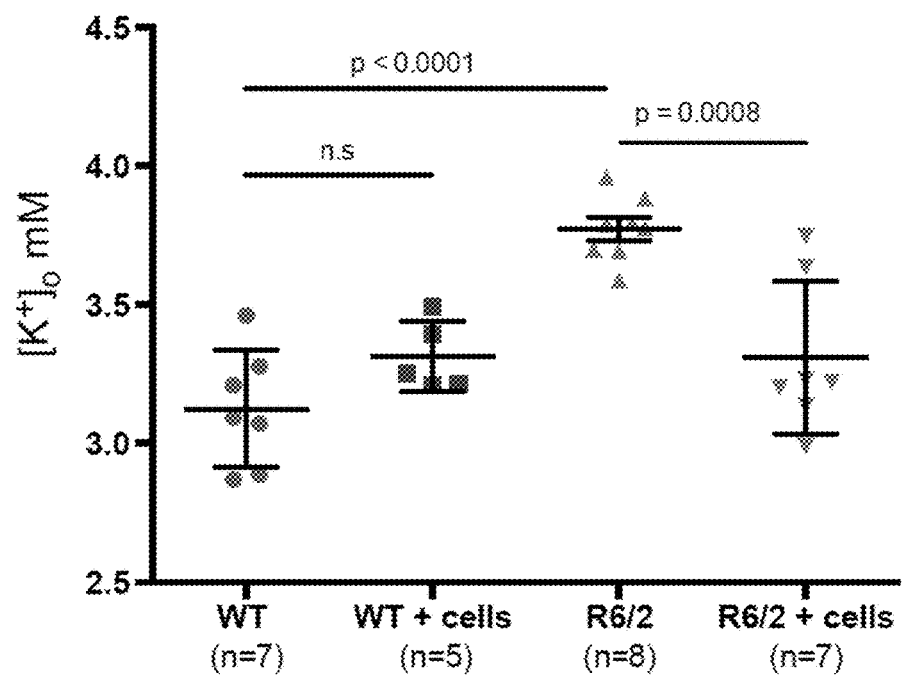
FIG. 7 illustrates that normal glial engraftment reduces interstitial K$^+$ levels in the R6/2 striatum. Potassium electrodes were used to measure the interstitial levels of striatal K$^+$ in both wild-type mice and their R6/2 littermates, with and without neonatal intrastriatal transplants of CD44-sorted human GPCs. Untreated R6/2 mice manifested significantly higher levels of interstitial K, which were restored to normal in R6/2 mice neonatally engrafted with hGPCs (p<0.01 by 1-way ANOVA). In contrast, hGPC engraftment did not influence the interstitial K$^+$ levels of wild-type mice.

Critically, whether that disease-associated elevation in extracellular K+ might then be attenuated by colonization with engrafted normal glial cells, and whether that might account for the partial restoration of normal membrane resistance and firing thresholds observed in R6/2 mice transplanted with normal glia was next investigated. This indeed proved to be the case, in that the R6/2 mice neonatally-engrafted intrastriatally with normal CD44+ hGPCs manifested significantly and substantially lower levels of striatal interstitial K+ than their unengrafted R6/2 littermates (p<0.01 by 1-way ANOVA) (FIG. 7). The reduction in interstitial K+ afforded by glial chimerization occurred only in R6/2 striata; wild-type mice transplanted with CD44+ GPCs manifested extracellular K+ levels no different from their untransplanted littermates.

Discussion of Examples 1-7

A number of recent reports have highlighted the contribution of glial cells to the pathogenesis of neurodegenerative disorders, most particularly in the spinal cord, in which glial pathology has been implicated in the course of amyotrophic lateral sclerosis (Di Giorgio et al., "Human Embryonic Stem Cell-Derived Motor Neurons are Sensitive to the Toxic Effect of Glial Cells Carrying an ALS-Causing Mutation," *Cell Stem Cell* 3 (6): 637-648 (2008); Di Giorgio et al., "Non-Cell Autonomous Effect of Glia on Motor Neurons in an Embryonic Stem Cell-Based ALS Model," *Nat. Neurosci.* 10 (5):608-614 (2007); Meyer et al., "Direct Conversion of Patient Fibroblasts Demonstrates Non-Cell Autonomous Toxicity of Astrocytes to Motor Neurons in Familial and Sporadic ALS," *Proc Natl Acad Sci USA*. 111 (2): 829-832 (2014); and Yamanaka et al., "Astrocytes as Determinants of Disease Progression in Inherited Amyotrophic Lateral Sclerosis," *Nat Neurosci.* 11 (3): 251-253 (2008), which are hereby incorporated by reference in their entirety). In this study, whether glia might contribute to the genesis and progression of a prototypic neurodegenerative disorder of the brain, Huntington Disease, was investigated. It was found that mice whose striata were engrafted with glial progenitors derived from mHtt-expressing hES cells (48Q) manifested significantly slowed motor learning compared to littermates chimerized with normal (18Q) GPCs derived from a normal sibling (FIG. 2). Using mice chimerized with human fetal striatal tissue-derived glia (73Q), applicants found that MSNs resident in that HD glial environment were significantly more excitable than those engrafted with control glia (23Q) glia, and manifested much of the range of neurophysiological abnormalities previously noted in HD MSNs, both in vitro (Shin et al., "Expression of Mutant Huntingtin in Glial Cells Contributes to Neuronal Excitotoxicity," *J Cell Biol.* 171:1001-1012 (2005), which is hereby incorporated by reference in its entirety) and within the striata of R6/2 HD mice (Klapstein et al., "Electrophysiological and Morphological Changes in Striatal Spiny Neurons in R6/2 Huntington's Disease Transgenic Mice," *J. Neurophysiol.* 86 (6): 2667-2677 (2001), which is hereby incorporated by reference in its entirety) (FIG. 3). On the basis of this glial-mediated recapitulation of HD-associated clinical and physiological pathology, whether the introduction of normal, healthy glia into the HD environment might slow disease progression or rescue aspects of disease phenotype was also investigated. This was found to be the case, in that striatal chimerization of R6/2 mice (120Q) with normal fetal human tissue-derived CD44-sorted glial cells was associated with a significantly and substantially increased survival (FIG. 5), a slower rate of motor deterioration, and improvement in at least some aspects of resident MSN physiology (FIG. 6). Together, these observations implicate astrocytic pathology in the pathogenesis and progression of HD, and suggest colonization of diseased striata with wild-type astroglia as a potential strategy for slowing disease progression in affected individuals.

Previous studies have highlighted the abnormal physiology of R6/2 mouse MSNs, which are characterized by relatively depolarized resting membrane potential, increased input resistances, and increased stimulus thresholds for EPSPs (Klapstein et al., "Electrophysiological and Morphological Changes in Striatal Spiny Neurons in R6/2 Huntington's Disease Transgenic Mice," *J. Neurophysiol.* 86 (6): 2667-2677 (2001), which is hereby incorporated by reference in its entirety). Chimerization of normal mouse striata with mutant Htt-expressing glia yielded many of these same electrophysiological abnormalities among co-resident MSNs. Immunodeficient but otherwise wild-type mice engrafted with mHtt-transduced human glia (73Q) manifested significantly increased excitability and input resistance relative to those engrafted with normal Htt (23Q)-transduced glia, as well as to unengrafted controls, and had response characteristics remarkably similar to those previously reported for R6/2 MSNs (Klapstein et al., "Electrophysiological and Morphological Changes in Striatal Spiny Neurons in R6/2 Huntington's Disease Transgenic Mice," *J. Neurophysiol.* 86 (6): 2667-2677 (2001), which is hereby incorporated by reference in its entirety).

As a corollary to the toxic effects of mHtt glia on normal MSNs, it was postulated that wild-type glia might be capable of rescuing pathology in R6/2 neurons. This prediction that was borne out with the increased net survival of R6/2 mice engrafted as adults with wild-type hGPCs, as well as by the improved physiology of R6/2 neurons in the wild-type glial striatal environment. In particular, while striatal neurons in R6/2×rag1$^{-/-}$ immunodeficient mice manifested the expected high input resistances and low spontaneous EPSP frequencies of R6/2 mice, those engrafted with normal CD44-sorted glia exhibited a significant reduction in input resistance and a significant increase in EPSP frequency, to levels not significantly different from wild-type controls (FIGS. 6A-6B).

A number of previous studies have reported the hyperexcitability of MSNs in HD, and several have pointed to defects in potassium conductance and potassium channel expression as contributing to both the hyperexcitability and increased input resistance of HD striatal neurons (Klapstein et al., "Electrophysiological and Morphological Changes in Striatal Spiny Neurons in R6/2 Huntington's Disease Transgenic Mice," *J. Neurophysiol.* 86 (6): 2667-2677 (2001) and Ariano et al., "Striatal Potassium Channel Dysfunction in Huntington's Disease Transgenic Mice," *J. Neurophysiol.* 93 (5): 2565-2574 (2005), which are hereby incorporated by reference in their entirety). Among other functions, astroglia are tasked with the uptake of $K^+$ from the brain's interstitial and synaptic spaces, into which $K^+$ flows in the setting of neuronal depolarization (Wang et al., "Astrocytes Modulate Neural Network Activity by Ca(2)+-Dependent Uptake of Extracellular $K^+$," *Sci Signal.* 5 (218): ra26 (2012) and Wang et al., "Bergmann Glia Modulate Cerebellar Purkinje Cell Bistability via $Ca^{2+}$-Dependent $K^+$ Uptake," *Proc Natl Acad Sci USA* 109 (20): 7911-6 (2012), which are hereby incorporated by reference in their entirety). If $K^+$ uptake is impaired, then the transmembrane gradient for $K^+$ is decreased, resulting in the increased excitability of local striatal neurons. Khakh and colleagues ascribed these findings to defects in astrocytic Kir 4.1 channel expression (Tong et al., "Astrocyte Kir4.1 Ion Channel Deficits Contribute to Neuronal Dysfunction in Huntington's Disease Model Mice," *Nat. Neurosci.* 17:694-703 (2014), which is hereby incorporated by reference in its entirety), while Levine and colleagues have highlighted the contribution of neuronal down-regulation of Kir2.1, Kir2.3 and Kv2.1 to the hyperexcitability of MSNs (Ariano et al., "Striatal Potassium Channel Dysfunction in Huntington's Disease Transgenic Mice," *J. Neurophysiol.* 93(5): 2565-2574 (2005), which is hereby incorporated by reference in its entirety). It seems unlikely that the loss of any single one of these channels would be sufficient to produce HD pathology, as they manifest considerable functional redundancy; indeed, the KCNJ10 gene that encodes Kir4.1 is mutated in the EAST syndrome, which is characterized by epilepsy, sensorineural deafness and renal tubular defects, but not by any HD-like pathology (Bockenhauer et al., "Epilepsy, Ataxia, Sensorineural Deafness, Tubulopathy, and KCNJ10 Mutations," *The New England Journal of Medicine* 360 (19): 1960-1970 (2009), which is hereby incorporated by reference in its entirety). Nonetheless, the coordinate down-regulation of a number of inwardly rectifying K+ channels across both neurons and glia might well be pathogenic. As such, applicants' observation of hyperexcitability by normal MSNs resident in an HD glial chimeric environment suggests that the pathological activation patterns of R6/2 MSNs might be substantially non-cell autonomous, and elicitable in otherwise normal neurons when those neurons are faced with defective local glial potassium homeostasis. Indeed, it was the apparent dependence of MSN hyperexcitability on glial K+ dysregulation (Tong et al., "Astrocyte Kir4.1 Ion Channel Deficits Contribute to Neuronal Dysfunction in Huntington's Disease Model Mice," *Nat. Neurosci.* 17 (5): 694-703 (2014), which is hereby incorporated by reference in its entirety)—as well as the coincident observation that HD-related muscle hyperexcitability similarly reflects poor K+ conductance (Waters et al., "Huntington Disease Skeletal Muscle is Hyperexcitable Owing to Chloride and Potassium Channel Dysfunction," *Proc Natl Acad Sci USA.* 110 (22): 9160-9165 (2013), which is hereby incorporated by reference in its entirety)—which suggested that local K+ gradients, and thus MSN firing thresholds, might be restored by colonization with normal glia.

Together, these data herald a significant role for glial dysfunction in HD pathogenesis. The mutant Htt human glial chimeric mouse model established here permitted evaluation of methods of neurotoxicity of mHtt glia on normal neostriatal neurons, and allowed the isolation and investigation of the non-cell autonomous component of HD neuropathology. Applicants established that a significant degree of protection may be offered to vulnerable mHtt-expressing neurons by an improved striatal glial environment, thus suggesting the therapeutic potential of a glial replacement strategy in HD. The finding that interstitial potassium levels are higher in R6/2 mice than wild-type littermates, and may be substantially normalized by chimerization of the HD striatum with normal glia (FIG. 7), further highlights the potential of glial cell replacement as a means of ameliorating HD-related pathology. Indeed, given the success in animal models of strategies developed to trigger the production of new striatal neurons from resident neural stem cells (Chmielnicki et al., "Adenovirally Expressed Noggin and Brain-Derived Neurotrophic Factor Cooperate to Induce New Medium Spiny Neurons from Resident Progenitor Cells in the Adult Striatal Ventricular Zone," *J. Neurosci.* 24 (9): 2133-2142 (2004), which is hereby incorporated by reference in its entirety), applicants have substantially extended the survival of R6/2 mice (Benraiss et al., "Sustained Mobilization of Endogenous Neural Progenitors Delays Disease Progression in a Transgenic Model of Huntington's Disease," *Cell Stem Cell* 12 (6): 787-799 (2013); Benraiss et al., "Cellular Therapy and Induced Neuronal Replacement for Huntington's Disease," *J. Am. Soc. Exper. Neuro Ther.* 8 (4): 577-590 (2011); and Cho et al., "Induction of Neostriatal Neurogenesis Slows Disease Progression in a Transgenic Murine Model of Huntington Disease," *J. Clin. Invest.* 117 (10): 2889-2902 (2007), which are hereby incorporated by reference in their entirety) and postulate that the combination of induced neuronal replacement with wild-type glial engraftment may be able to preserve function in the diseased HD striatum, and thereby provide meaningful therapeutic benefit.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed:

1. A method of treating frontotemporal dementia, said method comprising:
   selecting a subject having frontotemporal dementia; and
   administering to the selected subject a preparation of CD44+ astrocyte-biased glial progenitor cells at a dosage effective to treat the frontotemporal dementia in the subject.

2. The method of claim 1, wherein said glial progenitor cells of the preparation are A2B5+ and/or CD140a+.

3. The method of claim 1, wherein said preparation of glial progenitor cells is administered to the striatum, forebrain, brain stem, and/or cerebellum of the subject.

4. The method of claim 1 further comprising:
   administering one or more reagents capable of inducing medium spiny neuron addition in conjunction with said administering of the preparation of glial progenitor cells.

5. The method of claim 4, wherein said one or more reagents is selected from the group consisting of brain-derived neurotrophic factor, noggin, neurotrophin-4 ("NT-4"), insulin-like growth factor-1, or a combination thereof.

6. The method of claim 1, wherein the subject is human.

7. The method of claim 1, wherein the glial progenitor cells are human glial progenitor cells.

8. The method of claim 1, wherein the glial progenitor cells are derived from fetal tissue, embryonic stem cells, or induced pluripotent stem cells.

* * * * *